(12) United States Patent
Nanami et al.

(10) Patent No.: US 6,876,450 B2
(45) Date of Patent: Apr. 5, 2005

(54) LASER ABSORPTION SPECTRAL DIFFRACTION TYPE GAS DETECTOR AND METHOD FOR GAS DETECTION USING LASER ABSORPTION SPECTRAL DIFFRACTION

(75) Inventors: Masaya Nanami, Zama (JP); Takeshi Tsukamoto, Hadano (JP)

(73) Assignee: Anritsu Corporation, Tokyo (JP)

( * ) Notice: Subject to any disclaimer, the term of this patent is extended or adjusted under 35 U.S.C. 154(b) by 204 days.

(21) Appl. No.: 10/239,960

(22) PCT Filed: Jan. 30, 2002

(86) PCT No.: PCT/JP02/00688

§ 371 (c)(1),
(2), (4) Date: Sep. 25, 2002

(87) PCT Pub. No.: WO02/061402

PCT Pub. Date: Aug. 8, 2002

(65) Prior Publication Data

US 2003/0076500 A1 Apr. 24, 2003

(51) Int. Cl.⁷ .............................................. G01N 21/00
(52) U.S. Cl. ...................................................... 356/437
(58) Field of Search .................................. 356/436–440

(56) References Cited

U.S. PATENT DOCUMENTS 5,767,976 A * 6/1998 Ankerhold et al. ......... 356/437

FOREIGN PATENT DOCUMENTS

| JP | 58-198746 A | 11/1983 |
| JP | 62-66142 A | 3/1987 |
| JP | 1-280272 A | 11/1989 |
| JP | 7-103887 A | 4/1995 |

* cited by examiner

Primary Examiner—Gregory J. Toatley, Jr.
Assistant Examiner—Amanda Merlino
(74) Attorney, Agent, or Firm—Frishauf, Holtz, Goodman & Chick, P.C.

(57) ABSTRACT

A laser absorption spectroscopy type gas detection device is provided in which a light source device emits a laser beam containing a light component having a wavelength corresponding to an absorption spectrum of gas to be detected. A concave mirror has a reflecting surface to reflect and condense the laser beam reflected by material body existing in an advancing direction of the laser beam. A light receiver is disposed at the condensing position by the concave mirror and outputs an electric signal for detecting whether the gas to be detected is present in a vicinity of the material body. An adjustment mechanism freely moves and adjusts a relative position of the concave mirror and the light receiver in accordance with a distance to the material body such that the light receiver is positioned at the condensing position.

17 Claims, 12 Drawing Sheets

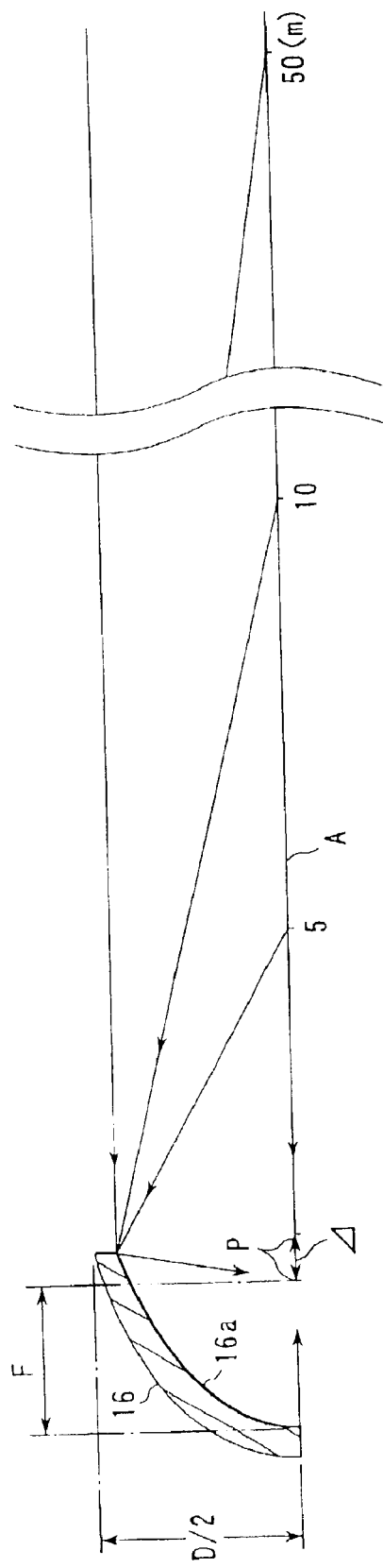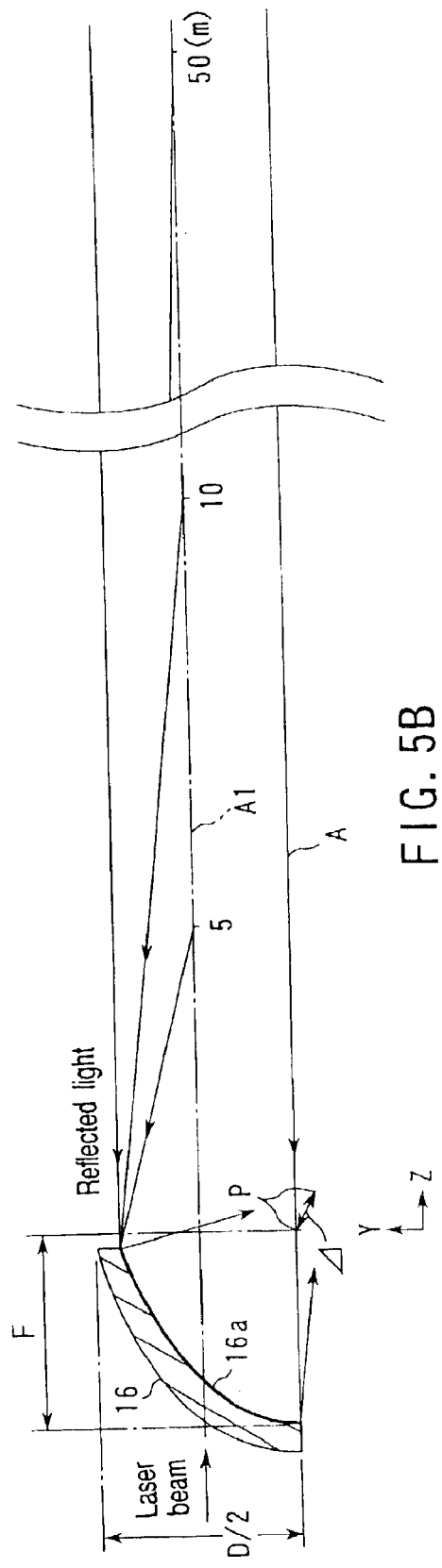

LASER ABSORPTION SPECTRAL DIFFRACTION TYPE GAS DETECTOR AND METHOD FOR GAS DETECTION USING LASER ABSORPTION SPECTRAL DIFFRACTION

This application is a U.S. National Phase Application under 35 USC 371 of International Application PCT/JP02/00688 filed Jan. 30, 2002.

TECHNICAL FIELD

The present invention relates to a laser absorption spectroscopy type gas detecting device and a gas detecting method using laser absorption spectroscopy, and in particular, to a laser absorption spectroscopy type gas detecting device which aims to be compact and lightweight and can be made to be easy to carry when a gas leak of city gas, at a chemical plant or the like is to be detected by using the light absorption characteristics of gas, and to a gas detecting method using laser absorption spectroscopy including focusing of the device.

BACKGROUND ART

As is well-known, gases such as methane, carbon dioxide, acetylene, and ammonia have an absorption band absorbing light of a specific wavelength in accordance with the rotation of constituent molecules of the respective gases or vibration between constituent atoms.

For example, in the case of methane gas, the gas has absorption bands absorbing light of specific wavelengths such as a 1.65 μm band, a 3.3 μm band, and a 7.7 μm band.

FIG. 12 is a graph showing light absorption spectrum characteristics of methane gas at a wavelength of 1.65 μm.

Namely, as shown in FIG. 12, in accordance with the light absorption spectrum characteristics of methane gas, it can be understood that the light intensity at a wavelength of 1.65 μm is damped in a dip-shape.

Further, a laser absorption spectroscopy type gas detecting device applies a laser beam to a gas generating place from a remote position by using such light absorption characteristics of the gas, and detects the existence of gas optically.

By using such a laser absorption spectroscopy type gas detecting device, gas leakage of, for example, city gas, at a chemical plant or the like can be detected from far away.

It should be noted that, generally, such a laser absorption spectroscopy type gas detecting device has been required to aim for compactness and a lighterweight as a portable type, so as to be easily carried into a site at the time of a gas leak or at the time of inspection.

FIG. 13 is a side sectional view showing a structure of a conventional laser absorption spectroscopy type gas detecting device 50 disclosed in Jpn. Pat. Appln. KOKAI Publication No. 7-103887.

Namely, as shown in FIG. 13, in the laser absorption spectroscopy type gas detecting device 50, a convex-shaped condenser lens 52 is provided at a front surface of a housing 51.

At the central portion of the condenser lens 52, a light source portion 53 formed from a laser diode (LD) module is provided.

At a remote position of a predetermined distance, a laser beam of a predetermined wavelength band is emitted, from the light source portion 53, into a space at which it is supposed that gas to be detected exists.

Then, the laser beam emitted from the light source portion 53 is reflected by a material body having the property of reflecting light, such as the wall of a building existing within the distance which the external laser beam can reach, and returns to the laser absorption spectroscopy type gas detecting device 50.

After this reflected light is condensed by the condenser lens 52 of the laser absorption spectroscopy type gas detecting device 50, the light is received by a light receiver 54 provided at the inner portion of the housing 51.

Here, if gas to be detected exists at the front portion of the external reflecting material body, because the laser beam emitted from the light source section 53 passes through the gas to be detected, the light component of a specific wavelength of the laser beam is absorbed by the gas to be detected.

Therefore, in the reflected light, the light intensity at the light component of this specific wavelength is damped by the light absorption characteristics of the gas to be detected.

Accordingly, the light receiving level at the light component of this specific wavelength at the light receiver 54 is also damped.

On the other hand, when gas to be detected does not exist at the front portion of the reflecting material body, damping of the light intensity at the light component of the specific wavelength by the light absorption characteristics of the gas to be detected does not occur. Therefore, damping of the light receiving level at the light component of this specific wavelength at the light receiver 54 does not also occur.

In this way, the light receiver 54 outputs an electric signal for detecting whether gas to be detected exists at the front portion of the reflecting material body, in accordance with the damping degree of the light component having a wavelength corresponding to the light absorption spectrum of the gas to be detected.

Further, a signal processing portion (not shown) carries out signal processing for detecting the presence/absence of the gas to be detected, on the basis of the electric signal corresponding to the light-receiving state from the light receiver 54.

However, in the conventional laser absorption spectroscopy type gas detecting device 50 as described above, the condenser lens 52 used in the device is large (for example, the diameter is 12 cm, the thickness is 3 cm, and the weight is 1 kg or more).

Therefore, the housing 51, holding the condenser lens 52 in the state of preventing optical axis offset or the like, requires rigidity strength of that extent, and the weight of the housing 51 itself becomes heavy.

In accordance therewith, because the entire device of the conventional laser absorption spectroscopy type gas detecting device 50 is large and heavy, there are the problems that transport thereof cannot be easily carried out and the device is unsuitable for portable use.

Further, in the conventional laser absorption spectroscopy type gas detecting device 50 as described above, the light source section 53 of a predetermined size (for example, the diameter is 4 cm) is provided at the central portion including the optical axis of the condenser lens 52. Therefore, the effective condensing area of the condenser lens 52 decreases, and there is a problem that the condensing efficiency tends to deteriorate.

Due to such an arrangement of the light source section 53, in order to ensure the effective condensing area of the condenser lens 52, it is unavoidable that the condenser lens 52 itself is large.

Further, the conventional laser absorption spectroscopy type gas detecting device 50 as described above has a structure in which the gas to be detected is detected in a range of distances (measuring distances) to the place which is apart by about 50 m from the closest to the device.

Therefore, the focal distance of the condenser lens 52 requires a predetermined length in accordance with the measuring distance.

In accordance therewith, in the conventional laser absorption spectroscopy type gas detecting device 50 as described above, because the length from the condenser lens 52 to the light receiver 54 must be long, it is unavoidable that the housing 51 becomes large and heavy.

Here, if a short focal lens is used as the condenser lens 52 in order to make the housing 51 compact, due to the condenser lens 52 being thicker, the condenser lens 52 becomes heavier.

On the other hand, if a long focal lens is used as the condenser lens 52, the length of the housing 51 becomes long and heavy.

FIG. 14 is a side sectional view showing another structure of the conventional laser absorption spectroscopy type gas detecting device 50 disclosed in Jpn. Pat. Appln. KOKAI Publication No. 7-103887.

In FIG. 14, structural portions which are the same as those of the laser absorption spectroscopy type gas detecting device 50 of FIG. 13 are denoted by the same reference numerals, and description thereof will be omitted.

Namely, in the conventional laser absorption spectroscopy type gas detecting device 50 as shown in FIG. 14, a focal point adjustment mechanism 60 is provided within the housing 51.

As described above, the laser absorption spectroscopy type gas detecting device 50 detects the presence/absence of gas, without contact, with a predetermined distance range.

In accordance with a change of the measuring distance, the image formation position of the reflected light condensed by the condenser lens 52 changes.

Here, the focal point adjustment mechanism 60 detects the image formation position of the reflected light, and carries out focal point adjustment such that the light receiver 54 is positioned on the image formation position.

Namely, in this focal point adjustment mechanism 60, after one portion of the reflected light condensed by the condenser lens 52 is branched off by a half mirror 61, the light is irradiated to an image sensor 63 via a lens 62.

The branched-off light detected on the image sensor 63 moves in accordance with the focal point position of the light receiver 54.

Here, due to moving means 64 being controlled in accordance with the detected position at the image sensor 63, the light receiver 54 is moved in an optical axis direction.

The focal adjustment mechanism 60 thereby can carry out focal point adjustment such that the image formation position of the reflected light condensed by the condenser lens 52 is positioned on the light receiving surface of the light receiver 54.

By the way, in the conventional laser absorption spectroscopy type gas detecting device 50 as described above, because the laser beam emitted toward the gas to be detected is invisible light, there is the problem that the user cannot easily confirm by visual observation what position the laser beam is irradiated to.

Therefore, even if the conventional laser absorption spectroscopy type gas detecting device 50 has the focal point adjustment mechanism 60 as described above, there has been the problem that the gas to be detected cannot be reliably detected if the irradiated position of the laser beam is unclear.

Here, a laser absorption spectroscopy type gas detecting device, which is configured such that a user confirms an irradiated position of laser beam by visual observation due to a laser pointer emitting visible laser beam being provided, is known.

However, in such a laser absorption spectroscopy type gas detecting device, the device as the laser pointer must be separately installed, and further there are the problems that the weight becomes heavier and costs increase.

Note that this laser pointer is for a user to confirm an irradiated position of laser beam on a reflecting material body by visual observation, and focal point adjustment within the device cannot be immediately carried out.

Further, the focal point adjustment mechanism 60 has a large number of parts and needs an arithmetic processing portion for adjusting the focal point position. Therefore, there is the problem that the structure is complex and reducing the cost for the entire device cannot be attempted.

DISCLOSURE OF INVENTION

The present invention is achieved in consideration of the problems as described above, and the object thereof is to provide a laser absorption spectroscopy type gas detecting device which can aim to be made compact and light-weight and can be easily carried.

Further, the present invention is achieved in consideration of the problems as described above, and the object thereof is to provide the laser absorption spectroscopy type gas detecting device which is easily carried by being made compact and lightweight, and in which visual confirmation of the irradiated position of laser beam and focal point adjustment at interior can be easily carried out, and a gas detecting method using a laser absorption spectroscopy including focal point adjustment of the device.

In accordance with a first aspect of the invention, there is provided a laser absorption spectroscopy type gas detecting device comprising:

a housing (2) having a light transmitting portion (2b);

a light source device (5) which is disposed within the housing and emits a laser beam containing a light component having a wavelength corresponding to an absorption spectrum of a gas to be detected, to an exterior via the light transmitting portion;

concave mirrors (6, 16) which are disposed within the housing and have reflecting surfaces (6a, 16a) at which the laser beam, emitted to the exterior by the light source device, is reflected by a material body existing in an advancing direction of the laser beam and having a property of reflecting light and returns via the light transmitting portion, is reflected and condensed on a predetermined condensing position (P); and a light receiver (7) which is disposed at the predetermined condensing position by the concave mirror within the housing, and outputs an electric signal for detecting whether the gas to be detected exists or not at a front portion of the material body, in accordance with a degree of damping of the light component having the wavelength corresponding to the absorption spectrum of the gas to be detected, by receiving the laser beam which returns via the light transmitting portion.

In accordance with a second aspect of the invention, there is provided a laser absorption spectroscopy type gas detecting device according to the first aspect, wherein the light source device (5) comprises:

a semiconductor laser module (5a) which is provided out of an optical path of the laser beam returning via the light transmitting portion, and emits the laser beam containing the light component having the wavelength corresponding to the absorption spectrum of the gas to be detected;

a fiber collimator (5c) which is provided at a position in front of the concave mirror (6), and directs the laser beam emitted from the semiconductor laser module toward the exterior along an optical axis (A) positioned at a center of the concave mirror; and an optical fiber (5b) which leads the light emitted from the semiconductor laser module out to the fiber collimator.

In accordance with a third aspect of the invention, there is provided a laser absorption spectroscopy type gas detecting device according to the first aspect, wherein the semiconductor laser module (5a) is provided at rear portion of a central position of the concave mirror (16); and an opening portion (16b), through which the laser beam emitted from the semiconductor laser module (5a) is made to pass, is formed at the central position of the concave mirror.

In accordance with a fourth aspect of the invention, there is provided a laser absorption spectroscopy type gas detecting device according to the first aspect, further comprising:

moving means (11, 21) for freely moving and adjusting a relative position of the concave mirrors (6, 16) and the light receiver (7);

wherein it is configured such that the relative position can be moved and adjusted in accordance with a distance to the material body (9) having the property of reflecting external light, in order that the light receiver is positioned at the condensing position (P) by the concave mirror.

In accordance with a fifth aspect of the invention, there is provided a laser absorption spectroscopy type gas detecting device according to the first aspect, wherein the reflecting surface (6a) of the concave mirror has a specific paraboloid shape or ellipsoid based shape corresponding to settings of a predetermined diameter D and a predetermined focal point distance F.

In accordance with a sixth aspect of the invention, there is provided a laser absorption spectroscopy type gas detecting device according to the first aspect, wherein the reflecting surface (16a) of the concave mirror has a paraboloid shape or an ellipsoid based shape of an upper half or a lower half of a specific paraboloid or ellipsoid corresponding to the settings of a predetermined diameter D and a predetermined focal point distance F.

In accordance with a seventh aspect of the invention, there is provided a laser absorption spectroscopy type gas detecting device comprising:

a housing (2) having a light transmitting portion (2b);

a light source device (5) which is disposed within the housing and emits laser beam containing a light component having a wavelength corresponding to an absorption spectrum of a gas to be detected, to an exterior via the light transmitting portion;

concave mirrors (6, 16) which are disposed within the housing and has reflecting surfaces (6a, 16a) at which the laser beam, emitted to the exterior by the light source device, is reflected by a material body existing in an advancing direction of the laser beam and having a property of reflecting light and returns via the light transmitting portion, is reflected and condensed at a predetermined condensing position (P);

a light receiver (7) which can be disposed at the condensing position by the concave mirror within the housing, and outputs an electric signal for detecting whether the gas to be detected exists or not at a front portion of the material body, in accordance with a degree of damping of the light component having the wavelength corresponding to the absorption spectrum of the gas to be detected, by receiving the laser beam which returns via the light transmitting portion;

a visible light source (30) which can be disposed at the condensing position by the concave mirror within the housing, and, by emitting visible light toward the concave mirror, emits the visible light to the exterior via the light transmitting portion on a path in an opposite direction of the laser beam reflected by the material body and returning via the light transmitting portion, and forms a predetermined image which can be visually confirmed on the material body; and moving means (31, 41) for moving the disposed positions of the light receiver and the visible light source so as to be replaced by each other.

In accordance with an eighth aspect of the invention, there is provided a laser absorption spectroscopy type gas detecting device recited in the seventh aspect, wherein the moving means (31, 41) are configured so as to freely move and adjust a relative position of the concave mirrors (6, 16) and the light receiver (7).

In accordance with a ninth aspect of the invention, there is provided a laser absorption spectroscopy type gas detecting device according to the seventh aspect, wherein the moving means (31, 41) are configured such that the light receiving surface of the light receiver (7) and the light emitting surface of the visible light source (30) can be replaced by each other on substantially the same position with respect to the concave mirrors (6, 16).

In accordance with a tenth aspect of the invention, there is provided a laser absorption spectroscopy type gas detecting device recited in the seventh aspect, wherein the light source device (5) comprises:

a semiconductor laser module (5a) which is provided out of an optical path of the laser beam returning via the light transmitting portion, and emits the laser beam containing the light component having the wavelength corresponding to the absorption spectrum of the gas to be detected;

a fiber collimator (5c) which is provided at a position in front of the concave mirror (6), and directs the laser beam emitted from the semiconductor laser module toward the exterior along an optical axis (A) positioned at a center of the concave mirror; and an optical fiber (5b) which leads the light emitted from the semiconductor laser module out to the fiber collimator.

In accordance with a eleventh aspect of the invention, there is provided a laser absorption spectroscopy type gas detecting device according to the seventh aspect, wherein the semiconductor laser module (5a) is provided at a rear portion of the central position of a concave mirror (16); and an opening portion (16b), through which the laser beam emitted from the semiconductor laser module (5a) is made to pass, is formed at the central position of the concave mirror.

In accordance with a twelfth aspect of the invention, there is provided a laser absorption spectroscopy type gas detecting device according to the seventh aspect, wherein the reflecting surface of the concave mirror has specific paraboloid shape or ellipsoid based shape corresponding to settings of a predetermined diameter D and a predetermined focal point distance F.

In accordance with a thirteenth aspect of the invention, there is provided a laser absorption spectroscopy type gas detecting device recited in the seventh aspect, wherein the reflecting surface of the concave mirror has a paraboloid shape or an ellipsoid based shape of a upper half or a lower half of a specific paraboloid or ellipsoid corresponding to the settings of a predetermined diameter D and a predetermined focal point distance F.

In accordance with a fourteenth aspect of the invention, there is provided a gas detecting method utilizing laser absorption spectroscopy, comprising:

a step of emitting laser beam containing a light component having a wavelength corresponding to an absorption spectrum of a gas to be detected, to an exterior by a light source device (5);

a step of making the laser beam, emitted to the exterior from the light source device (5) and reflected by a material body existing in an advancing direction of the laser beam and having a property of reflecting light and returning, be reflected and condensed on a predetermined condensing position (P) by concave mirrors (6, 16) having reflecting surfaces (6a, 16a);

a step of detecting whether or not the gas to be detected exists at a front portion of the material body, in accordance with a degree of damping of the light component having the wavelength corresponding to the absorption spectrum which the gas to be detected has, by receiving, at a light receiver (7) opposing the concave mirror, the laser beam condensed on the condensing position (P) by the concave mirrors (6, 16) and reflected by the material body and returning; and a step of making, in advance of the detecting step, a predetermined image, which enables viewing of an irradiated position of the laser beam emitted from the light source device (5) to the exterior be formed on the material body, by opposingly disposing a visible light source (30) emitting visible light instead of the light receiver which opposes the concave mirror and by emitting the visible light from the visible light source to the exterior.

In accordance with a fifteenth aspect of the invention, there is provided a laser absorption spectroscopy type gas detecting device according to the fourteenth aspect, further comprising:

a step of changing a relative position of the concave mirrors (6, 16) and the visible light source (30) such that an image-forming state of a predetermined image which can be viewed on the material body by the visible light from the visible light source (30) is optimal, wherein the light receiving surface of the light receiver can be positioned at the condensing position of the reflecting light by the concave mirror, and focal point adjustment corresponding to a distance to the material body having the property of reflecting the external light is possible.

In accordance with the first through fifteenth aspects, the laser beam emitted from the light source 5 is incident on the concave mirror 6 as the laser beam which passes through the gas to be measured and is scattered and reflected by the material body 9 having a property of reflecting light and returns.

This concave mirror 6 condenses the laser beam, scattered and reflected at the material body 9 having a property of reflecting light and returning, on the light receiving surface of the light receiver 7.

At this time, the presence/absence of the gas to be measured can be detected by differences in the amounts of light which the light receiver 7 receives.

Further, due to the light source device 5 being configured such that only the fiber collimator 5c is disposed in front of the concave mirror 6, the decrease in the laser beam, scattered and reflected at the material body 9 having a property of reflecting light and returning, can be a minimum.

Further, the semiconductor laser module 5a of the light source portion 5 is disposed at the rear portion of the concave mirror 16, and the emitted light from the semiconductor laser module 5a may be directly emitted from the opening portion 16c at the center of the concave mirror 16.

Further, the condensing position of the concave mirror 6 changes in accordance with a change in the distance to the material body 9 having the property of reflecting light, i.e., a change in the measuring range of the device. However, by relatively moving the concave mirror 6 and the light receiver 7 by the moving means 11, the light receiving surface of the light receiver 7 can be positioned on the condensing position corresponding to the measuring distance.

Further, the light receiver 7 disposed in accordance with the concave mirror 6 detects the reflected light condensed at the concave mirror 6. However, due to the visible light source 30 being replaced by the light receiver 7 portion by the moving means 31, the visible light from the visible light source 30 is reflected at the concave mirror 6 and can be irradiated to the material body 9 having the property of reflecting light, in a way opposite to the way at the time of receiving light.

This visible light which can be viewed on the material body 9 having the property of reflecting light is in an image-forming state corresponding to the distance (measuring distance) from the device to the material body 9 having the property of reflecting light.

Further, a focal point position can be matched by moving the relative position of the visible light source 30 with respect to the concave mirror 6 by the moving means 31.

Thereafter, due to the visible light source 30 and the light receiver 7 being replaced again by the moving means 31, the relative position of the light receiver 7 with respect to the concave mirror 6 can be set in a state in which the focal points match by restoring the positional relationship.

Note that the condensing position of the reflected light which the concave mirror 6 condenses in accordance with changes in the measuring distance of the device.

However, in the present invention, the concave mirror 6 and the visible light source 30 (light receiver 7) are relatively moved by the moving means 31, and the positional relationship of the visible light source 30 and the light receiver 7 is switched.

Accordingly, the light receiving surface of the light receiver 7 can be positioned at the condensing position corresponding to the measuring distance, and focal point adjustment can be easily carried out.

BRIEF DESCRIPTION OF DRAWINGS

FIG. 5A is a diagram showing condensing characteristics of a concave mirror formed from a half portion of a paraboloid used in a third embodiment of the laser absorption spectroscopy type gas detecting device according to the present invention;

FIG. 5B is a diagram showing condensing characteristics of a concave mirror formed from a half portion of a paraboloid used in a fourth embodiment of the laser absorption spectroscopy type gas detecting device according to the present invention;

BEST MODE FOR CARRYING OUT OF THE INVENTION

Hereinafter, respective embodiments of the present invention will be described by using the figures.

(First Embodiment)

Figure 1:
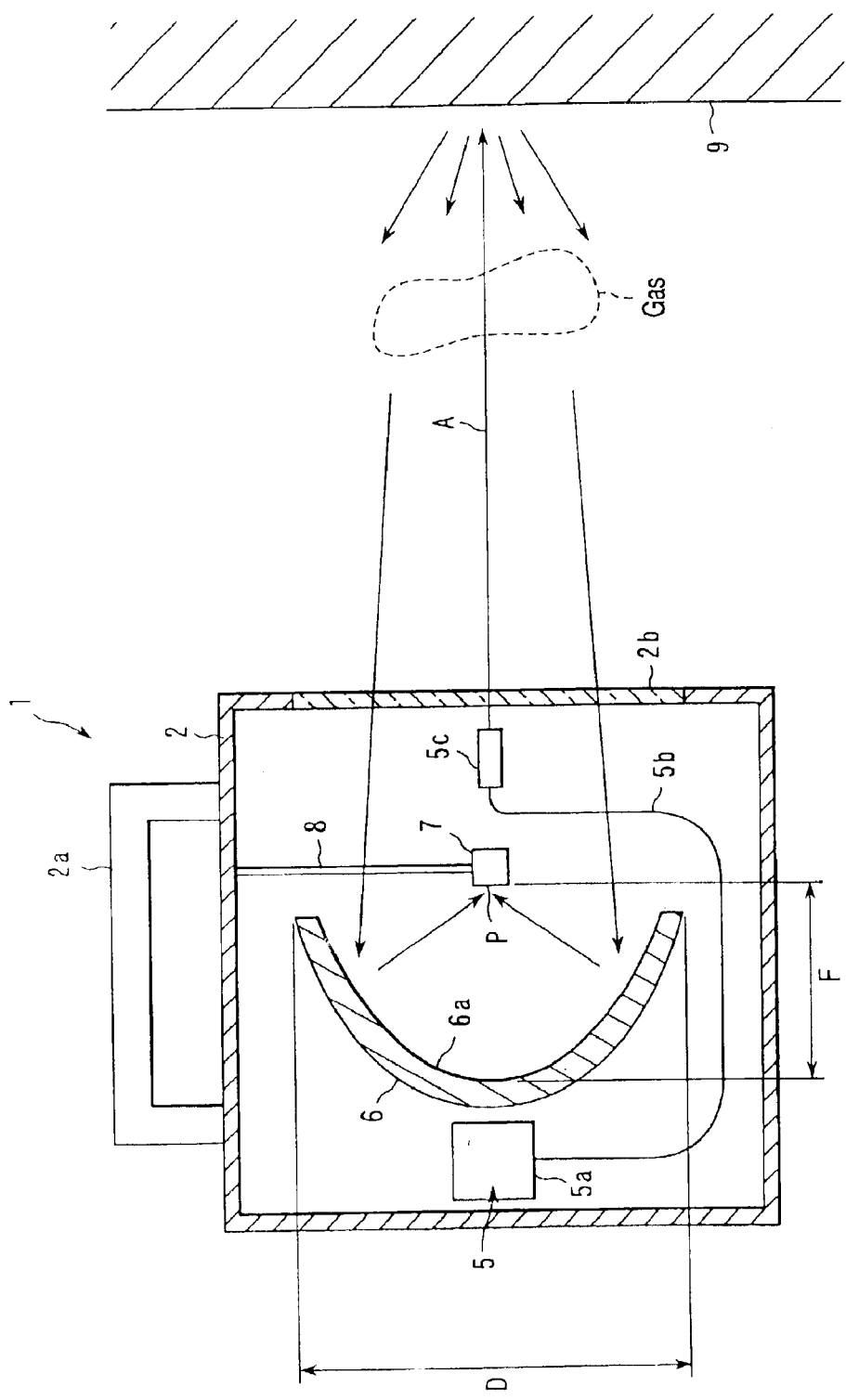
FIG. 1 is a side sectional view showing a configuration of a first embodiment of a laser absorption spectroscopy type gas detecting device according to the present invention.

FIG. 1 is a side sectional view showing a configuration of a first embodiment of a laser absorption spectroscopy type gas detecting device according to the present invention.

Namely, as shown in FIG. 1, a laser absorption spectroscopy type gas detecting device 1 is schematically configured to include a light source device 5, a concave mirror 6, and a light receiver 7, at an interior of a housing 2.

Here, the housing 2 is formed in, for example, a rectangular parallelepiped box shape, and is freely carried by providing a handle 2a for carrying at the upper portion thereof.

At the front surface portion of the housing 2, a light transmitting portion 2b, in which a transparent resin body, a glass or the like is fitted into an opening portion formed so as to be a size equivalent to or greater than a diameter D of the concave mirror 6, is formed.

Further, the light source device 5 is formed from a semiconductor laser module 5a, an optical fiber 5b, and a fiber collimator 5c, and emits to an exterior, via the light transmitting portion 2b, laser beam containing a wavelength component matching an absorption spectrum which is particular to the gas to be detected.

When the gas to be detected is methane gas, the semiconductor laser module 5a configuring the light source device 5 is formed by providing a semiconductor laser (LD) generating laser beam of a wavelength band covering the absorption wavelength of 1.65 μm, light emission driving means thereof, temperature controlling means and the like.

The optical fiber 5b, for leading out the laser beam generated by the LD, is connected to the semiconductor laser module 5a.

The optical fiber 5b leads the laser beam from the semiconductor laser module 5a out to the fiber collimator 5c.

In this way, the laser beam from the semiconductor laser module 5a is emitted to the exterior via the light transmitting portion 2b by the fiber collimator 5c.

The fiber collimator 5c is supported by three supporting rods (not shown) spreading radially at constant intervals in a plurality of angular directions, for example, every 120°, at the front surface of the housing 2.

Note that, at the emitting side of the semiconductor laser module 5a, an optical isolator or the like preventing return light to the LD side is provided.

Further, the concave mirror 6 is provided within the housing 2 in a state in which the center of the concave mirror 6 coincides with an optical axis A of the laser beam emitted to the exterior via the light transmitting portion 2b by the light source device 5 (the fiber collimator 5c).

The concave mirror 6 has a reflecting surface 6a whose cross-section is formed, for example, in a paraboloid or an ellipsoid based shape.

A mirror which is formed from, for example, plastic, aluminum, glass or the like, and in which aluminum or gold is deposited or plated in a mirror surface form on the reflecting surface 6a, is used as the concave mirror 6.

The reflecting surface 6a of the concave mirror 6 has a specific paraboloid or ellipsoid based shape corresponding to settings of the diameter D and the focal point distance F, and reflects the light incident on the reflecting surface 6a via the light transmitting portion 2b, and condenses the light on a predetermined condensing position P.

Namely, the laser beam emitted to the exterior via the light transmitting portion 2b by the fiber collimator 5c is scattered (reflected) by a material body 9 having the property of reflecting external light, such as a wall, a ceiling, ground, grass, snow or the like in the vicinity of a space in which the gas to be detected is assumed to exist, and returns to the device side.

Then, the laser beam, which is reflected by the material body 9 having the property of reflecting external light and returns, is condensed at the condensing position P via the light transmitting portion 2b as incident light on the concave mirror 6.

Note that, generally, even if laser beam is scattered by the material body 9 having the property of reflecting light, the reflected light therefrom maintains a certain extent of directivity.

Therefore, in order to condense the laser beam, which is reflected by the material body 9 having the property of reflecting external light and returns, as effectively as possible by the concave mirror 6, it is preferable that the central position of the concave mirror 6 is provided so as to coincide with the optical axis A of the laser beam emitted to the exterior by the fiber collimator 5c.

The light receiver 7 is provided at the condensing position P by the concave mirror 6.

The light receiver 7 is disposed such that the light receiving surface thereof is directed toward the center of the concave mirror 6, and receives the light condensed by the concave mirror 6, i.e., the laser beam which is reflected by the material body 9 having the property of reflecting external light and returns.

Here, the light receiver 7 is supported by a tubular supporting member 8 at the interior of the housing 2.

Further, a light receiving signal from the light receiver 7 is led out to the exterior of the housing 2 through the interior of the supporting member 8.

The light source device 5 and light receiver 7 are led out to an unillustrated processing device via an unillustrated connector provided at the housing 2.

This processing device drive-controls the light source device 5, and carries out processing for detecting the presence/absence of the gas to be detected in the space (place) which is an object of measurement, on the basis of the light receiving signal from the light receiver 7.

Operation of the laser absorption spectroscopy type gas detecting device 1 according to the configuration will be described.

At the time of inspecting a gas leak or at the time of detecting (reporting) a leak, the user carries the laser absorption spectroscopy type gas detecting device 1 to a place separated by a predetermined distance and close to a site where it is supposed that gas is leaking.

Thereafter, the user, by operating the laser absorption spectroscopy type gas detecting device 1, emits the laser beam for measuring from the fiber collimator 5c of the light source device 5 via the light transmitting portion 2b toward the exterior place where it is supposed that there is a gas leakage.

The laser beam is emitted in a beam shape on the optical axis A, and passes through the space at which it is supposed that the gas to be detected exists, and is reflected by the material body 9 having the property of reflecting light such as a wall of a building or the like in the vicinity of the space, and returns again to the side of the laser absorption spectroscopy type gas detecting device 1 side.

At this time, the laser absorption spectroscopy type gas detecting device 1 side can carry out measuring work for detecting gas in a non-contact manner at a remote place which is a predetermined distance (about 2 to 50 m) away from the place where it is supposed that there is a gas leak.

Then, the laser beam, reflected by the material body 9 having the property of reflecting external light and returning again to the side of the laser absorption spectroscopy type gas detecting device 1, is incident on the concave mirror 6 within the housing 2 via the light transmitting portion 2b.

The concave mirror 6 reflects the incident light, and condenses the light on the light receiver 7 disposed at the condensing position P within the housing 2.

At this time, at the place where it is supposed that there is a gas leak, if an atmosphere of the gas to be detected actually exists, laser beam of a predetermined wavelength is absorbed by the gas.

Therefore, in the light receiving level detected by the light receiver 7, damping occurs at the predetermined wavelength portion.

When the light receiving level at a predetermined wavelength absorbed by the aforementioned gas, among the light receiving levels detected at the light receiver 7, is relatively damped, the processing device determines that the gas actually exists, and notifies and outputs the fact that the leaked gas has been detected, by a meter display, a warning sound or the like.

The laser absorption spectroscopy type gas detecting device 1 having the configuration is a structure in which the laser beam, which is reflected by the material body 9 having the property of reflecting external light and returns again to the side of the laser absorption spectroscopy type gas detecting device 1, is efficiently condensed by using the concave mirror 6. Therefore, making the device compact and lightweight can be attempted.

For example, when there is an effective area which is similar to that of the condenser lens 52 described in the conventional art, the diameter D of the concave mirror 6 may be 6 cm which is half as compared to the conventional art, and the device can be made small to a large extent.

Further, the concave mirror 6 can be formed so as to be thin in accordance with the form thereof. Thus, for example, when the constituent body is made of plastic, it suffices that the weight is about 50 g. Therefore, the concave mirror 6 can be made much lighter as compared with the condenser lens 52 described in the conventional art.

In accordance therewith, an attempt can be made to greatly make the housing 2 compact and lighter.

Further, the concave mirror 6 can shorten the focal point distance F as compared with that of the condensing lens 52 described in the conventional art.

For example, when the concave mirror 6 is configured from a paraboloid mirror and the diameter D is equal to 10 cm and the measuring distance range is 2 through 50 m, the focal point distance F can be greatly shortened to 50 mm.

In this way, it can be attempted to make the housing 2 more compact, and in particular, the length of the housing 2 in the optical axis A direction can be shortened.

At this time, as described above, because the concave mirror 6 itself is lightweight and the focal point distance thereof can be shortened, the housing 2 itself can be formed to have a rigidity to the extent of fixing and holding the position of the concave mirror 6.

Thus, the housing 2 can be manufactured from, for example, plastic or the like, and it can be attempted to make the entire device even lighter.

In this way, because making the laser absorption spectroscopy type gas detecting device 1 of the configuration compact and lightweight can be attempted, carrying of the device is easy, and the operation of emitting laser beam for measuring toward an atmosphere of external gas can be easily carried out.

In particular, because methane gas used for a city gas is lighter than air, if a gas leak occurs indoors, the leaked gas easily stays at the ceiling portion or the like.

However, as described above, because making the laser absorption spectroscopy type gas detecting device 1 of the structure compact and lightweight can be attempted, the operation of emitting laser beam for measuring toward the atmosphere of the gas staying at the ceiling portion or the like can be easily carried out.

It should be noted that, because the fiber collimator 5c and the light receiver 7 configuring the light source device 5 are disposed ahead of the concave mirror 6 for each, a predetermined amount of the light incident on the concave mirror 6 is damped.

However, in the laser absorption spectroscopy type gas detecting device 1 of the configuration, the semiconductor laser module 5a, in which various types of parts are built-in and for which a predetermined size is necessary, is disposed at a position away from the region where the light incident on the concave mirror 6 passes through.

In accordance therewith, there is a structure in which only the compact fiber collimator 5c for emitting laser beam to the exterior and the compact light receiver 7 disposed at the condensing by the concave mirror 6 are disposed in the region at which the light incident on the concave mirror 6 passes through. Therefore, damping of the light incident on the concave mirror 6 can be suppressed as much as possible.

Namely, at present, the fiber collimator 5c can be formed compactly at a size whose diameter is 5 mm or less.

Further, the light receiver 7 also can be formed compactly at a size whose diameter is 10 mm or less.

(Second Embodiment)

Figure 2:
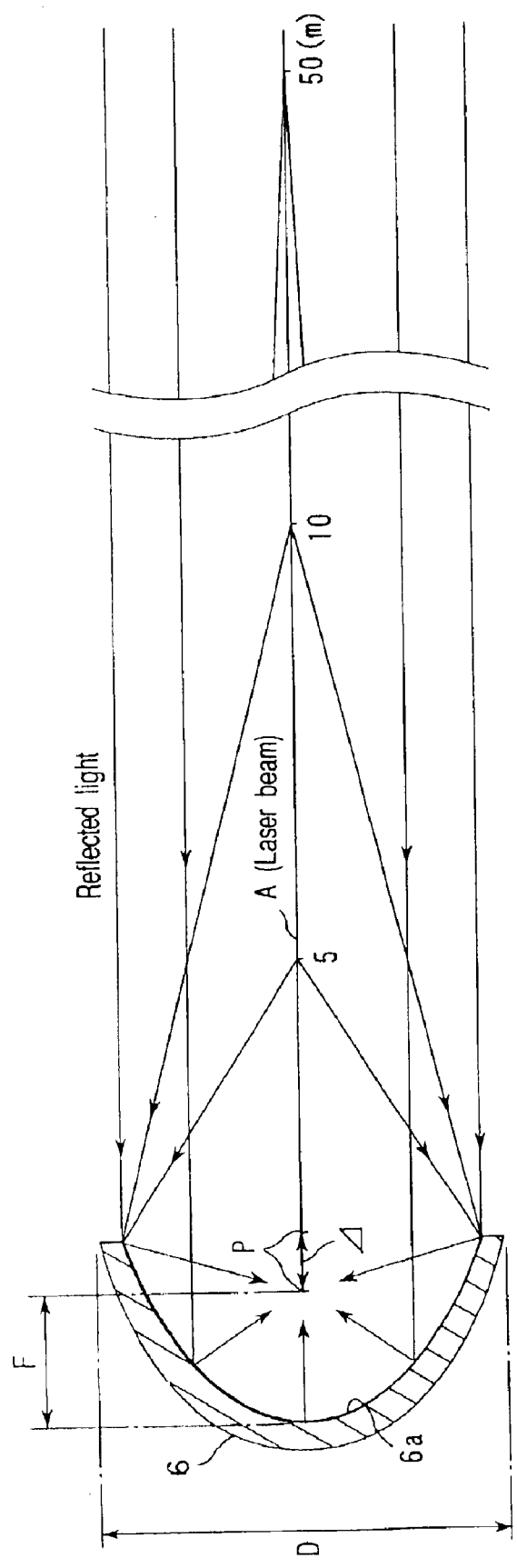
FIG. 2 is a diagram showing condensing characteristics of a concave mirror which is a paraboloid in FIG. 1.

FIG. 2 is a view showing the condensing characteristics of the concave mirror 6.

In the concave mirror 6 of the illustrated example, in the same way as described above, the reflecting surface 6a has a specific paraboloid shape or ellipsoid based shape corresponding to the settings of the diameter D and the focal length F.

In this concave mirror 6, as illustrated, the condensing position P is different for each measuring distance.

As shown in FIG. 2, the condensing position P by the concave mirror 6 has the characteristic that, the further away the measuring distance, i.e., the further the position of the material body 9 having the property of reflecting light with respect to the laser absorption spectroscopy type gas detecting device 1, the closer to the position of the focal point distance F.

In contrast to this, the condensing position P by the concave mirror 6 has the characteristic that, the nearer to the measuring distance, the further away from the focal point distance F along the optical axis A.

Namely, the condensing position P by the concave mirror 6 has an offset amount Δ in accordance with the measuring distance.

Figure 3:
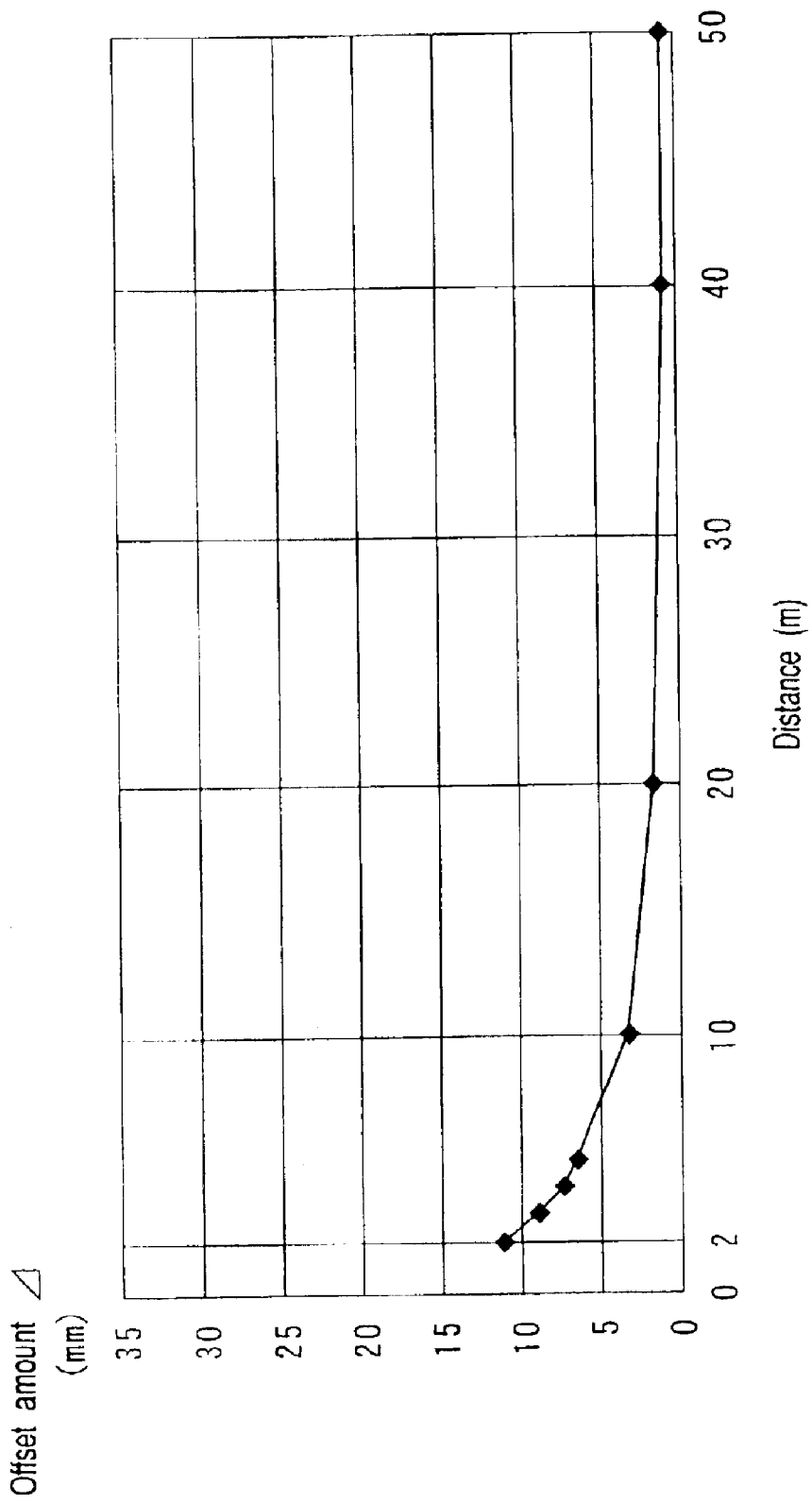
FIG. 3 is a diagram showing the relationship of measuring distance—condensing position of the concave mirror in FIG. 1.

FIG. 3 is a diagram showing the relationship of the measuring distance and the offset amount Δ of the condensing position P of the concave mirror 6.

Namely, as shown in FIG. 3, in the measuring distance range of 2 m to 50 m in the laser absorption spectroscopy type gas detecting device 1, the offset amount Δ of the condensing position P with respect to the focal point distance F is, at 2 m, a large value of 11.3 m, whereas the offset amount Δ is, at 50 m, a small value of 0.7 m.

However, if there is the offset amount Δ corresponding to the measuring distance at the condensing position P by the concave mirror 6, offset arises also in the amount of received light at the light receiver 7.

Thus, because the closer the measuring distance, the smaller the amount of received light at the light receiver 7, there is the concern that the sensitivity of gas detection will deteriorate.

Thus, the second embodiment is configured such that the amount of received light at the light receiver 7 is increased and the sensitivity of gas detection is improved by correcting the offset amount Δ of the condensing position P by the concave mirror 6.

Figure 4:
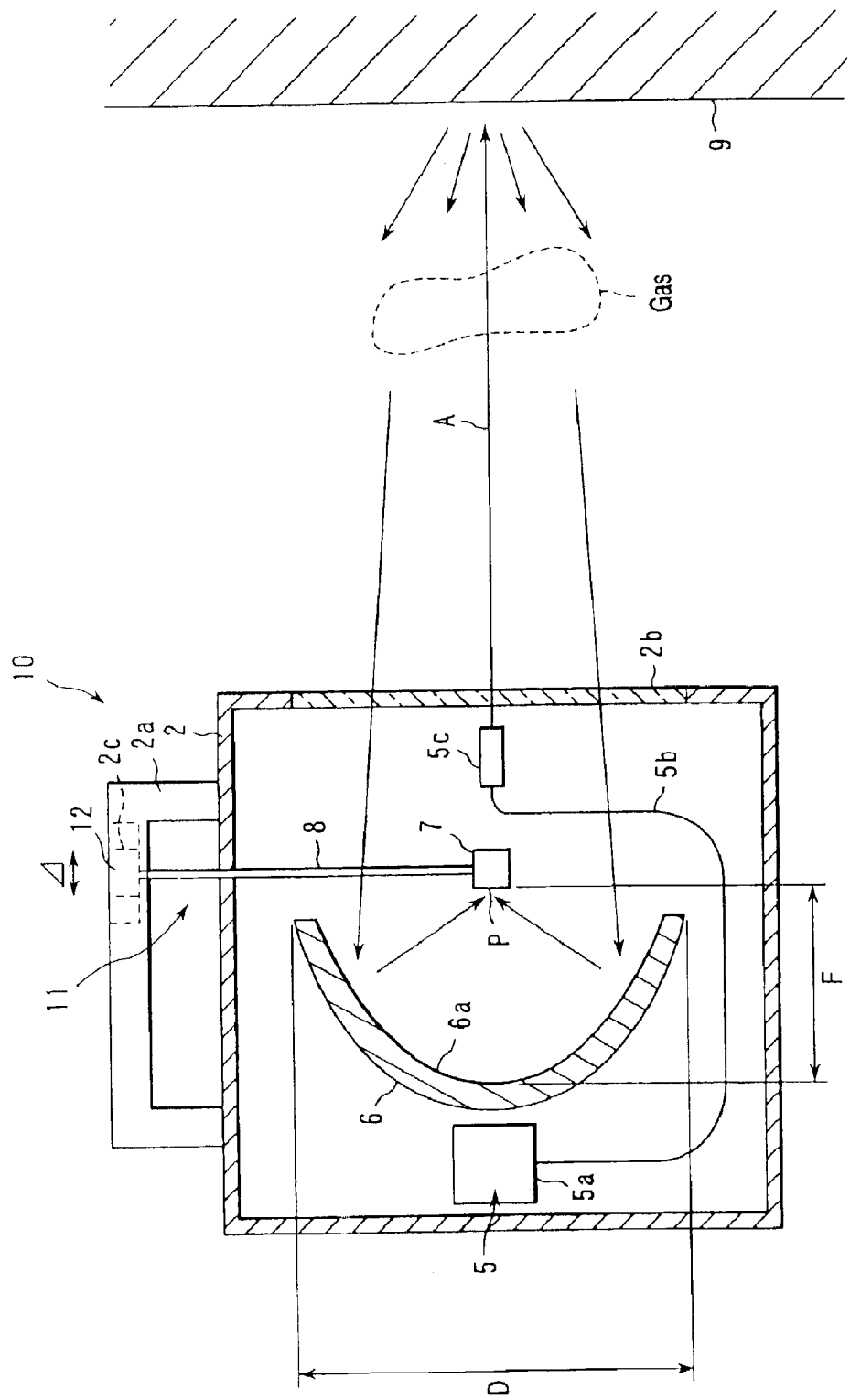
FIG. 4 is a side sectional view showing a configuration of a second embodiment of the laser absorption spectroscopy type gas detecting device according to the present invention.

FIG. 4 is a side sectional view showing a configuration of a laser absorption spectroscopy type gas detecting device 10 according to the second embodiment of the present invention.

In FIG. 4, structural parts which are the same as those of the laser absorption spectroscopy type gas detecting device of FIG. 1 described above are denoted by the same reference numerals, and description thereof will be omitted.

Namely, as shown in FIG. 4, in the laser absorption spectroscopy type gas detecting device 10 according to the second embodiment, an adjustment mechanism (moving means) 11 for moving the light receiver 7 along the optical axis A direction is provided.

The moving means 11 is configured from an operating lever 12 for moving the supporting member 8 of the light receiver 7 along the optical axis A.

In this case, the supporting member 8 passes through the housing 2 and is extended out up to the handle 2a portion which is formed along the direction of the optical axis A.

Further, the operating lever 12 is provided in the interior of a guiding slot 2c provided in the handle 2a, so as to be movable along the direction of the optical axis A.

By providing the operating lever 12 at the interior of the handle 2a in this way, the user can operate the operating lever 12 while holding the laser absorption spectroscopy type gas detecting device 1.

Namely, the user, by operating the operating lever 12, can move the light receiving surface of the light receiver 7 to an optimal condensing position corresponding to the measuring distance.

Concretely, the user operates the operating lever 12 such that the light receiving level of the light receiver 7 is the highest at the time of the gas detection operation.

At this time, although the light receiving level of a predetermined wavelength is damped by the absorption characteristic of the gas, the light receiving level of the wavelengths at the both side portions of the absorption wavelength is not changed.

Accordingly, the user operates the operating lever 12 in a state in which the wavelength of the laser beam generated by the semiconductor laser module 5a is variable.

Then, the user, by stopping the operating lever 12 at the position at which the light receiving level of the light receiver 7 at the both side portions of the absorption wavelength is the highest, the light receiver 7 is positioned at the optimal condensing position corresponding to the measuring distance at this time.

Further, it is not limited to this. If the concentration of the gas to be detected does not fluctuate and the light receiving level of the light receiver 7 is stable, the user may operate the operating lever 12 such that the light receiving level of the light receiver 7 is the highest at the aforementioned predetermined wavelength.

In this case, changing of the wavelength of the laser beam can be easily carried out by changing the temperature of the semiconductor laser (LD) by controlling a temperature controlling means such as a Peltier element provided at the semiconductor laser module 5a.

The moving means 11 of the configuration is configured so as to move the light receiver 7 in the direction of the optical axis A.

In contrast to this, it may be configured such that the light receiver 7 is fixed at the housing 2 and the concave mirror 6 is moved along the optical axis A by the moving means 11.

In brief, if the moving means 11 is configured such that the concave mirror 6 and the light receiver 7 are relatively moved along the direction of the optical axis A, similar effects as described above can be obtained.

Further, the moving means 11 is not limited to a configuration manually operated by the user as described above.

For example, if the moving means 11 is configured by an actuator, the moving means 11 can be automatically controlled via the processing device.

In this case as well, the processing device may be configured such that, while the moving means 11 is moved, the moving means 11 is stopped at a position at which the maximum value of the light receiving level output from the light receiver 7 is detected.

(Third Embodiment)

FIG. 5A is a diagram showing the condensing characteristics of a concave mirror of another shape different from that described above.

Namely, as the concave mirror 16 as shown in FIG. 5A and used in a third embodiment, a reflecting surface 16a thereof has a shape of the upper half (or the lower half) of a specific paraboloid or ellipsoid corresponding to the settings of the diameter D and the focal point distance F.

This is simply a shape in which the concave mirror 6 described in the first and second embodiments is divided in two at the central axis portion.

In the case of using the concave mirror 16 as well, the light source device 5, in the same way as described above, can be configured by having the semiconductor laser module 5, the optical fiber 5b, and the fiber collimator 5c.

In this case, the fiber collimator 5c is disposed at the central position (the lower end position at the concave mirror 16 as shown in FIG. 5A) at which the concave mirror 6 is divided in two.

Further, in the same way, laser beam is emitted at the optical axis A by the fiber collimator 5c, and the reflected light is received at the light receiver 7 disposed at the condensing position P, and gas detection can be carried out.

This embodiment as well may be a structure in which the moving means 11 is provided in the same way as described above.

Namely, as a configuration in which the concave mirror 16 or the light receiver 7 is relatively moved in the direction of the optical axis A by the moving means 11, the light receiver 7 can be positioned at an optimal condensing position corresponding to the measuring distance, by moving the condensing position P within the range of the offset amount Δ.

(Fourth Embodiment)

FIG. 5B is a diagram showing the condensing characteristics when the position of emission of the laser beam is changed by using the concave mirror 16 similar to that of FIG. 5A.

In this case, the laser beam emitted from the unillustrated light source device 5 is preferably emitted from the central position, not the lower end, of the concave mirror 16.

As described above, even if the laser beam is scattered by the material body 9 having the property of reflecting external light, the light reflected therefrom has directivity to a certain extent.

Therefore, the illustrated optical axis A1 is configured so as to emit light from the central position of the concave mirror 16.

In this way, in the case of using the concave mirror 16 configured from the one-side half of a paraboloid or an ellipsoid, when the optical axis A1 of the laser beam emitted from the light source device 5 is positioned away at a predetermined distance from the optical axis A, the condensing position P by the concave mirror 16 is, as illustrated, a position which is displaced in an oblique direction from the focal point position F.

Figure 6:
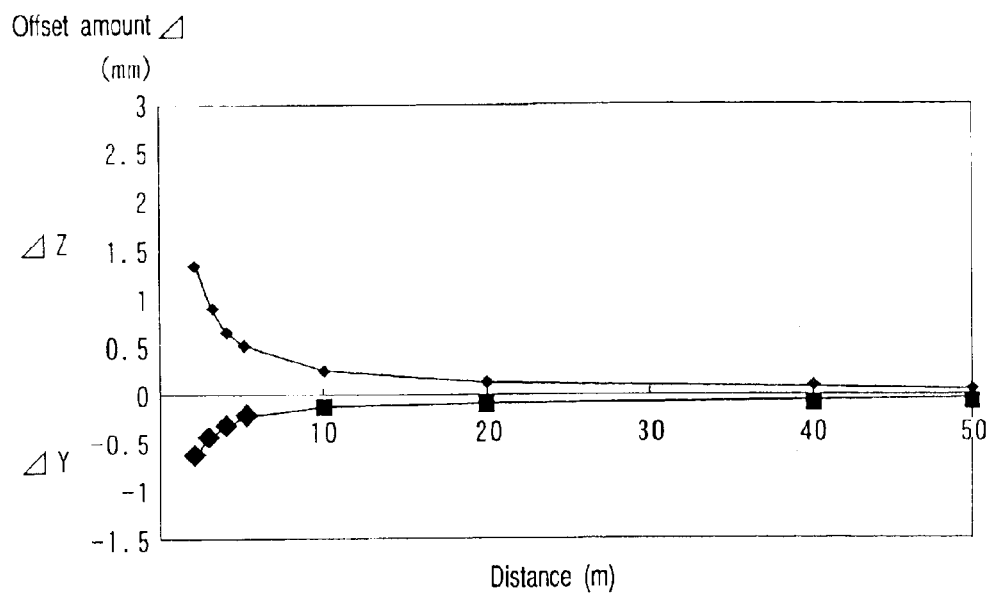
FIG. 6 is a diagram showing the relationship of measuring distance—condensing position when an optical axis is provided at the center of the concave mirror of FIG. 5B.

FIG. 6 is a diagram showing the relationship of the measuring distance and the condensing position offset amount Δ of the concave mirror 16 when the laser beam emitted from the light source device 5 is the optical axis A1.

As shown in FIG. 6, the further away the measuring distance, i.e., the position from the laser absorption spectroscopy type gas detecting device to the material body having the property of reflecting external light, the closer the condensing position P is to the position of the focal point distance F.

Conversely, it has the characteristic that the closer the measuring distance, the further away from the position of the focal point distance F obliquely in the direction −Y on the Y axis for the optical axis A1, and the direction +Z at the Z axis (in the direction of the optical axis A).

In the measuring distance range of 2 m to 50 m in the laser absorption spectroscopy type gas detecting device, the offset amount Δ of the condensing position P for the focal point distance F at 2 m is that ΔY is −0.69 mm and ΔZ is 1.36 mm, and the offset amount Δ at 50 m is that ΔY is −0.02 mm and ΔZ is 0.04 mm.

As shown in FIG. 5B, the offset amount Δ, when the optical axis A1 is disposed at the central position of the concave mirror 16, is that ΔZ is 1.36 mm at most, and the offset amount Δ is small as compared with that of the first embodiment.

Therefore, the light receiver 7 can be used by being fixedly disposed at the focal point position F portion.

Figure 7:
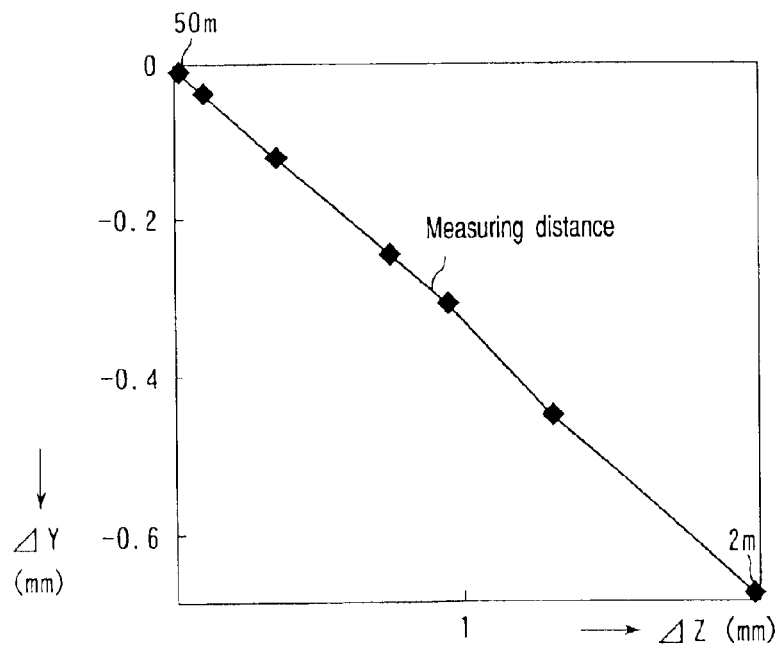
FIG. 7 is a diagram showing the relationship of the offset amounts ΔY, ΔZ of the concave mirror of FIG. 5B.

FIG. 7 is a diagram showing the relationship of the offset amount ΔY, ΔZ.

The offset amount of ΔY, ΔZ has a proportional relationship with respect to the respective measuring distances, and the offset amount is substantially positioned on a straight line as illustrated.

Accordingly, because the condensing position P is moved in an oblique direction with respect to the direction of the focal point position F, due to the concave mirror 16 and the light receiver 7 being relatively moved in this oblique direction, the condensing position P can be positioned on the light receiving surface of the light receiver 7.

Figure 8:
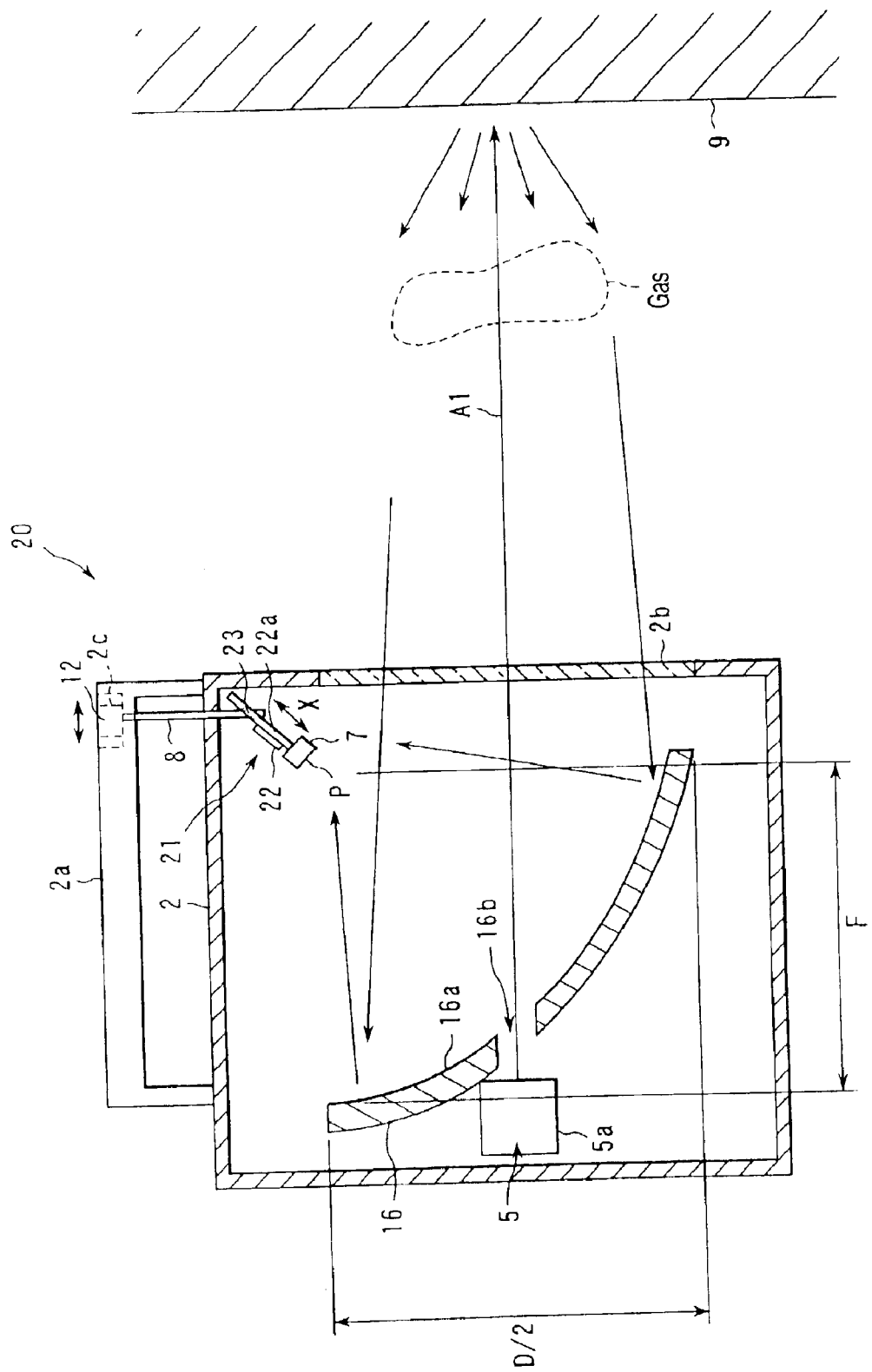
FIG. 8 is a side sectional view showing a configuration of the fourth embodiment of the laser absorption spectroscopy type gas detecting device according to the present invention using the concave mirror of FIG. 5B.

FIG. 8 is a side sectional view showing a configuration of a laser absorption spectroscopy type gas detecting device 20 according to the fourth embodiment.

Namely, the laser absorption spectroscopy type gas detecting device 1 as shown in FIG. 8 is schematically configured by providing the light source device 5, the concave mirror 16, and the light receiver 7 at the interior of the housing 2.

Note that the concave mirror 16 as shown in FIG. 8 is disposed such that the top and bottom of the concave mirror 16 of the structure as shown in FIG. 5B are opposite.

Here, the housing 2 is formed in, for example, a rectangular parallelepiped box shape, and is freely carried by providing the handle 2a for carrying at the upper portion thereof.

At the front surface portion of the housing 2, the light transmitting portion 2b, in which, for example, a transparent resin body, a glass or the like is fitted into an opening portion formed so as to be a size equivalent to or greater than a diameter D/2 of the concave mirror 16, is formed.

The light source device 5 is formed from only the semiconductor laser module 5a, and emits, via the light transmitting portion 2b and to the exterior, a laser beam of a wavelength matching an absorption spectrum which is particular to the gas to be detected.

When the gas to be detected is methane gas, the semiconductor laser module 5a configuring the light source device 5 is formed by providing a semiconductor laser (LD) generating laser beam of a wavelength band covering the absorption wavelength of 1.65 μm, light emission driving means thereof, temperature controlling means and the like.

As shown in FIG. 8, the light source device 5 is configured from only the semiconductor laser module 5a provided at the rear portion of the central position of the concave mirror 16.

Further, the laser beam is made to be directly emitted from the semiconductor laser module 5a.

This semiconductor laser module 5a emits the laser beam at the optical axis A1 via the opening portion 16b opened at the central position of the concave mirror 16.

In this case, a condenser lens (not shown), narrowing the laser beam generated by an LD into a beam shape, is provided.

Further, the light receiver 7 is supported so as to freely move by the moving means 21 in a direction corresponding to the offset amounts Δ (ΔY, ΔZ) in order to correct the aforementioned offset amounts Δ (ΔY, ΔZ).

This moving means 21 moves the light receiver 7 along the oblique direction X at which the offset amounts (ΔY, ΔZ) are combined.

Further, the moving means 21 is configured from a fixed and movable rail member 22 which holds the light receiver 7 and is for moving the light receiver 7 in the oblique direction X, the supporting member 8 which is interlocked with a rail 22a at the sliding side and extends to the handle 2a portion of the housing 2, and the operation lever 12 which can freely move in a guide slot 2c in the handle 2a.

Note that a slot 23, which the supporting member 8 is inserted through, is formed vertically.

In accordance with the laser absorption spectroscopy type gas detecting device 20 according to the fourth embodiment, the light receiver 7 can be positioned at a position away from the region of transmission of the reflected light. A reduction in the level of incidence, on the concave mirror 16, of the laser beam reflected by the material body 9 having the property of reflecting external light and returning, and accordingly, a decrease in the light receiving level at the light receiver 7, can be prevented.

In this way, due to a user moving-operating the operating lever 12 at the interior of the handle 2a along the direction of the optical axis A1, the light receiver 7 can be moved along the oblique direction X in which the offset amounts (ΔY, ΔZ) are combined, and the light receiver 7 can be positioned at the optimal condensing position P for the respective measuring distances.

At this time, the user can operate the operating lever 12 while holding the handle 2a of the laser absorption spectroscopy type gas sensing device 20.

Further, the user can move the light-receiving surface of the light receiver 7 to the condensing position P corresponding to the measuring distance, by operating the operating lever 12.

Concretely, in the same way as in the aforementioned embodiments, the operation lever 12 may be operated such that the light receiving level of the light receiver 7 is the highest at the time of the gas detecting operation.

The moving means 21 of the configuration is configured so as to move the light receiver 7 in the oblique direction X.

In contrast to this, even when there is a configuration in which the light receiver 7 is fixed on the housing 2 and the concave mirror 16 is moved along the oblique direction X by the moving means 21, operational effects similar to those described above can be obtained.

Note that, in the case of the configuration in which the concave mirror 16 is moved, strictly, in light of the relationship of the optical axis, it is preferable that the concave mirror 16 and the light source device 5 are integrally moved.

Further, it is not limited to the configuration in which the moving means 21 is manually-operated by the user as described above.

For example, it may be a configuration in which the moving means 21 is structured from an actuator, and the moving means 21 is automatically move-controlled by the processing device.

In this case as well, the processing device may be configured so as to, while moving the moving means 21, stop it at the position at which the maximum value of the light receiving level output from the light receiver 7 is detected.

In accordance with the first thorough fourth embodiments as described above, there is the configuration in which the laser beam, which, after passing through the gas to be detected, is reflected by the material body 9 having the property of reflecting external light and returns, is condensed at the concave mirror. Therefore, the focal point distance can be shortened by the concave mirror. Further, due to manufacturing being easy and due to attempts to make the device compact and lightweight, making the entire device compact and lightweight can be attempted, and a laser absorption spectroscopy type gas detecting device which is inexpensive and easy to carry can be realized.

Due to this laser absorption spectroscopy type gas detecting device being configured such that the laser beam from the light source device is emitted to the exterior via a small-sized fiber collimator disposed in front of the concave mirror, or via the opening portion of the concave mirror from the semiconductor laser module disposed at the rear portion of the concave mirror, a decrease in the light receiving level of the laser beam, which is reflected by the material body 9 having the property of reflecting external light received at the concave mirror and returns, can be prevented.

Further, due to the laser absorption spectroscopy type gas detecting device being configured such that the concave mirror and the light receiver are relatively movable in accordance with a change in the measuring distance by using the moving means, even if the measuring distance is different, the light receiving surface of the light receiver can be always positioned on the condensing position by the concave mirror. Therefore, stable gas detection can be always carried out at the optimal light receiving level.

(Fifth Embodiment)

Figure 9:
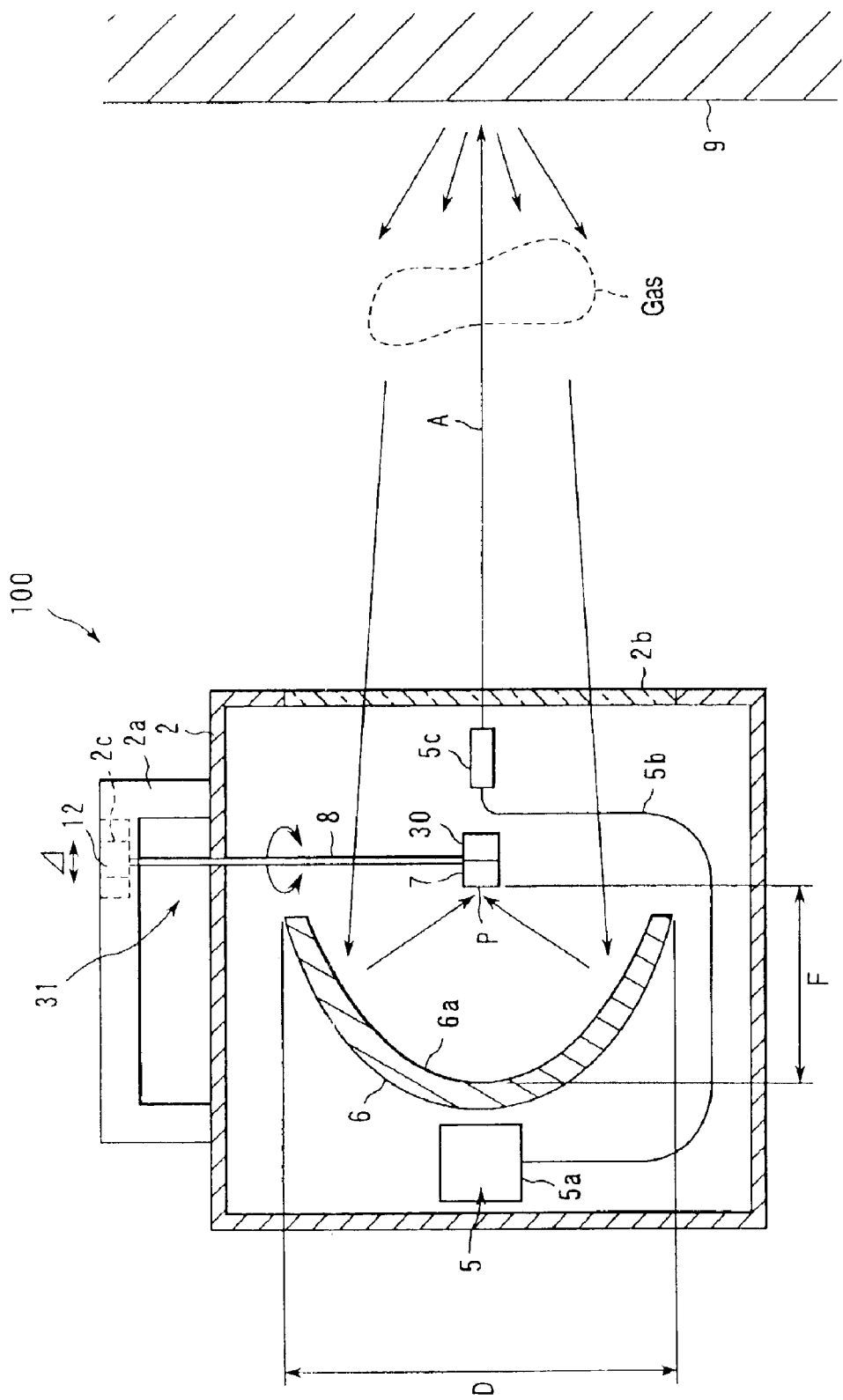
FIG. 9 is a side sectional view showing a configuration of a fifth embodiment of the laser absorption spectroscopy type gas detecting device according to the present invention.

FIG. 9 is a side sectional view showing a configuration of a fifth embodiment of the laser absorption spectroscopy type gas detecting device 10 according to the present invention.

In FIG. 9, the structural parts which are the same as those of the laser absorption spectroscopy type gas detecting device 1 of FIG. 1 and the laser absorption spectroscopy type gas detecting device 10 of FIG. 4 described above are denoted by the same reference numerals, and description thereof will be omitted.

Further, in this fifth embodiment as well, the relationship of the condensation characteristic of the concave mirror 6 shown in FIG. 2 and the offset amount Δ of the measuring distance and the condensing position P of the concave mirror 6 shown in FIG. 3 described above, is applied.

Namely, as shown in FIG. 9, in a laser absorption spectroscopy type gas detecting device 100 according to the fifth embodiment, moving means 31 is provided in order to carry out adjustment of the offset of the condensing position (focal point adjustment) by adjusting the irradiated state of the visible light from a visible light source 30 with respect to the material body 9 having the property of reflecting external light.

Namely, the moving means 31 is configured such that the light receiver 7 freely moves in the direction of the optical axis A in order to correct the offset amount of the condensing position P and increase the amount of light received at the light receiver 7.

In this moving means 31, the operating lever 12, for moving the supporting member 8 to which the light receiver 7 is attached along the optical axis A and for rotating the supporting member 8 in the direction perpendicular to this axial direction as will be described later, is provided at the interior of the guide slot 2c provided at the handle 2a of the housing 2.

The visible light source 30 is provided in order to move-adjust the condensing position by the concave mirror 6 on the basis of the image-forming state of the visible light on the material body 9 having the property of reflecting external light, by irradiating the visible light which becomes a pointer on the material body 9 having the property of reflecting external light, by using the characteristic of the concave mirror 6.

Namely, because the laser beam emitted from the light source device 5 is invisible light, a user cannot directly view the irradiated state of the laser beam with respect to the gas to be detected.

Therefore, due to the visible light being separately emitted from the visible light source 30 toward the material body 9 having the property of reflecting external light and being image-formed, the emitting direction and the position of the laser beam from the light source device 5 must be set in advance.

As described above, because the light receiver 7 is disposed at the condensing position P by the concave mirror 6, by using this arrangement relationship, the moving means 31 changes the emitting surface of the visible light source 30 to the position of the light receiving surface of the light receiver 7.

For example, a point light source is used as the visible light source 30, and a small lamp bulb of a flashlight or the like can be used.

For example, the light receiver 7 and the visible light source 30 are integrated such that the light receiving surface of the light receiver 7 and the emitting surface of the visible light source 30 are oriented in mutually opposite directions, and the central position thereof is supported by the supporting member 8.

Further, the moving means 31 is configured such that the light receiving surface of the light receiver 7 and the light emitting surface of the visible light source 30 can be replaced with each other at the same position, due to the supporting member 8 being rotatable in the direction perpendicular to the direction orthogonal to the axial direction by the operating lever 12.

Note that signal lines of the light receiver 7 and the visible light source 30 are configured so as to pass through the interior of the supporting member 8.

The gas detecting operation itself in accordance with the configuration is the same as that of the embodiments.

Here, confirmation of the laser irradiating position and the focal point adjusting operation using the visible light from the visible light source 30 before the aforementioned gas detecting operation will be described.

At the time of gas detection, first, the user directs the visible light source 30 toward the reflecting surface 6a side of the concave mirror 6 by rotating-operating the supporting member 8 of the moving means 31 by the operating lever 12.

Thereafter, if the visible light source 30 is turned on, the visible light from the visible light source 30 reaches the material body 9 having the property of reflecting external light via the concave mirror 6, and a predetermined image which the user can view is formed thereon.

Further, the user, by moving the operating lever 12 in the direction of the optical axis A, stops it at the position at which the image-forming state of the visible light on the material body 9 having the property of reflecting external light, is as close to a small spot shape as possible.

In this state, the visible light source 30 is positioned at the optimal condensing position by the concave mirror 6 corresponding to the distance to the material body 9 having the property of reflecting external light.

Accordingly, thereafter, due to the visible light source 30 and the light receiver 7 being switched by rotating the supporting member 8 of the moving means 31 by the operating lever 12, the user can position the light receiver 7 on the optimal condensing position corresponding to the measuring distance.

Further, thereafter, it suffices for the laser beam to be emitted, by driving the light source 5, toward the place at which it is supposed that the gas to be detected exists, and the laser beam, which is scattered and reflected at the material body 9 having the property of reflecting external light and which returns, to be condensed at the concave mirror 6, and to be received at the light receiver 7, and gas detection to be carried out.

In this state, the light receiver 7 is to be positioned at the optimal condensing position P corresponding to the measuring distance to the material body 9 having the property of reflecting external light, and matching with the condensing position can be easily carried out.

Further, because the visible light for visual confirmation emitted from the visible light source 30 is emitted with the optical axis A of the reflected light (laser beam) as the center by using the same concave mirror 6 as that for condensing at the time of gas detection, the light receiving surface of the light receiver 7 can be exactly positioned at the condensing position of the concave mirror 6, and focusing can be precisely carried out.

Although the moving means 31 of the configuration is configured so as to move the light receiver 7 in the direction of the optical axis A, conversely, there may be a configuration in which the light receiver 7 is fixed on the housing 2 and the concave mirror 6 is moved along the optical axis A by the moving means 31.

Namely, it suffices for the concave mirror 6 and the light receiver 7 to be relatively moved in the direction of the optical axis A.

Further, it is not limited to the configuration in which the moving means 31 is manually operated by a user as described above.

For example, it may be a configuration in which the moving means 31 is configured from an actuator and the moving means 31 is automatically controlled by the processing device.

In this case as well, the processing device may be configured so as to, while moving the moving means 31, stop it at the position at which the maximum value of the light receiving level output from the light receiver 7 is detected.

Further, in accordance with the fifth embodiment as described above, in the same way as in the first through fourth embodiments, a laser absorption spectroscopy type gas detecting device which aims to be compact and lightweight can be realized.

(Sixth Embodiment)

Figure 10:
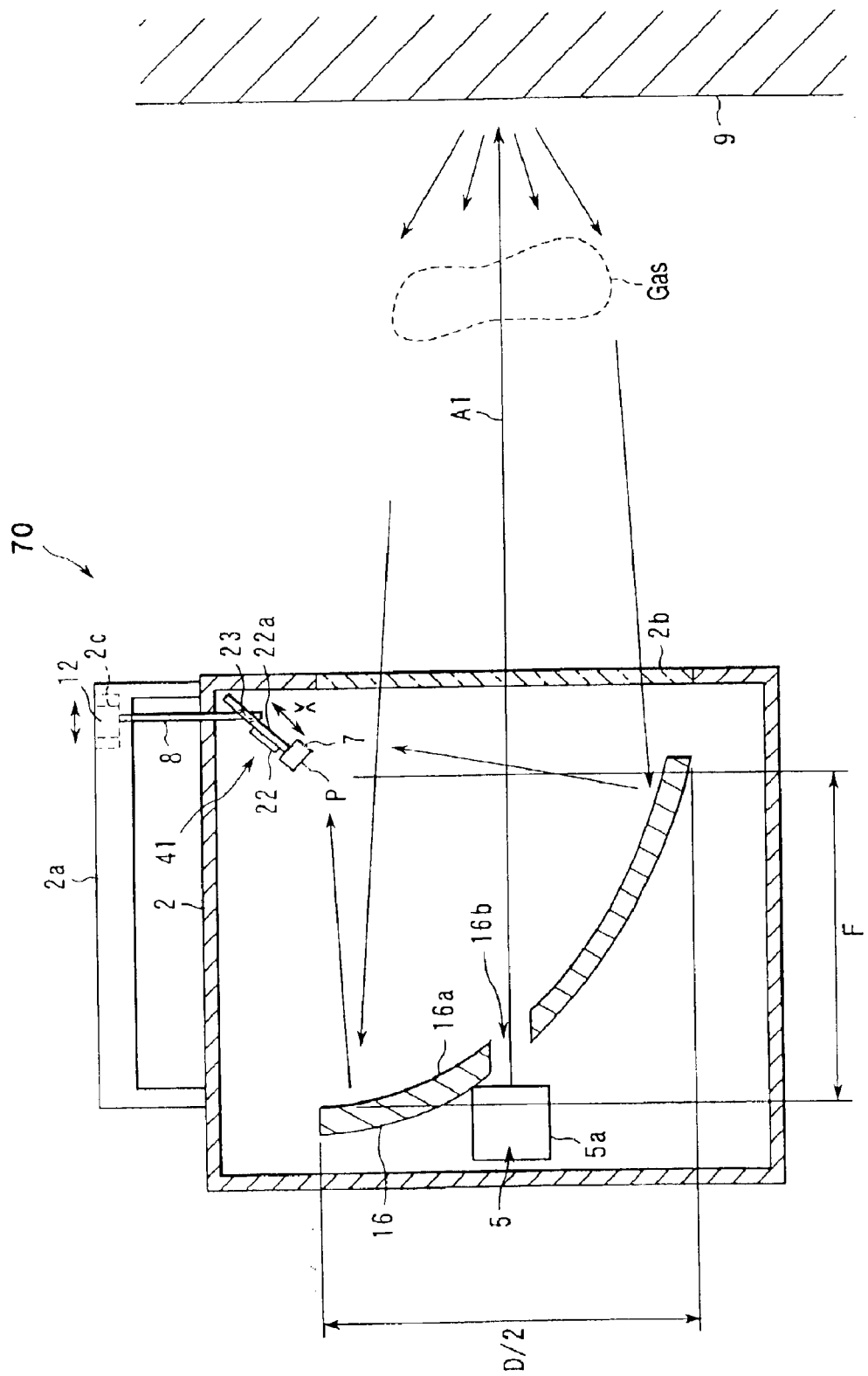
FIG. 10 is a side sectional view showing a configuration of a sixth embodiment of the laser absorption spectroscopy type gas detecting device according to the present invention.

FIG. 10 is a side sectional view showing a configuration of a laser absorption spectroscopy type gas detecting device 70 according to a sixth embodiment.

Figure 11:
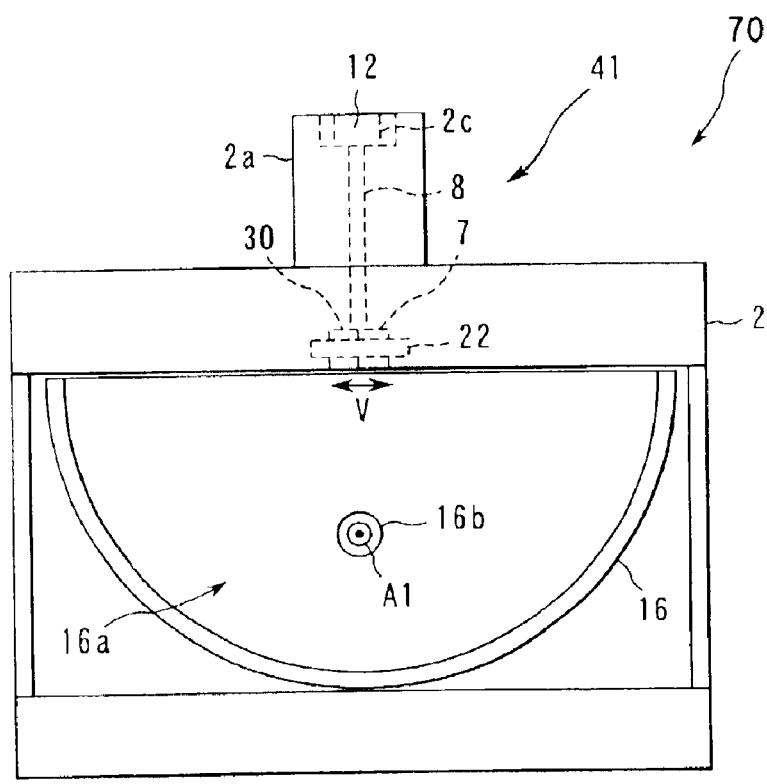
FIG. 11 is a front view showing a configuration of the sixth embodiment of the laser absorption spectroscopy type gas detecting device according to the present invention.
Figure 12:
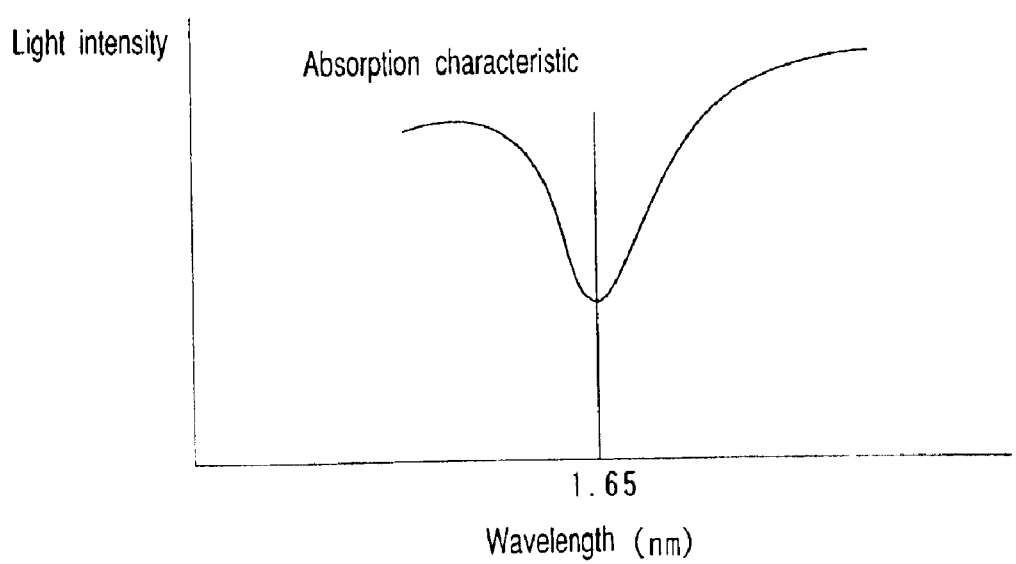
FIG. 12 is a diagram showing one example of an absorption spectrum characteristic curve of methane gas.
Figure 13:
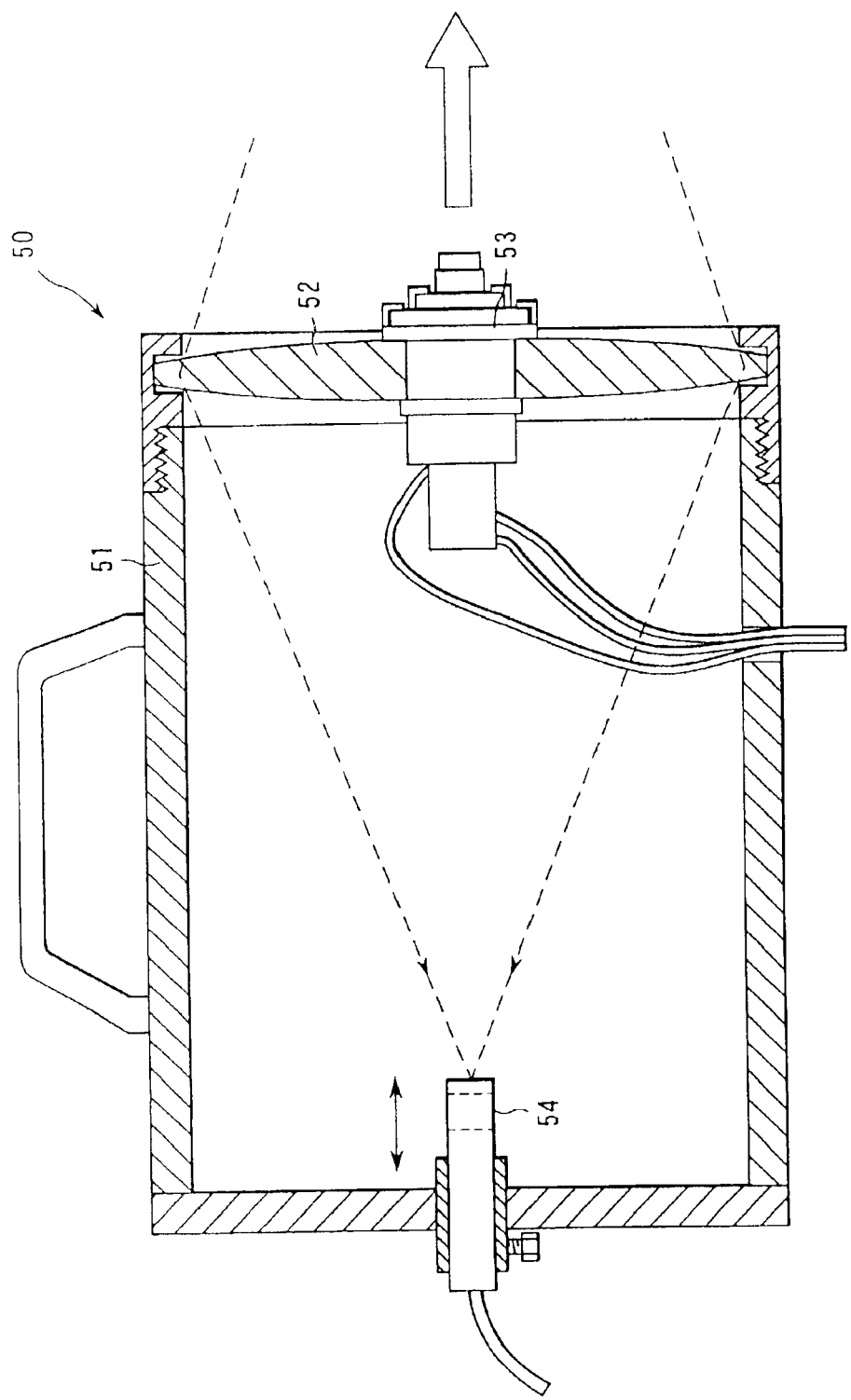
FIG. 13 is a side sectional view showing a configuration of a conventional laser absorption spectroscopy type gas detecting device.
Figure 14:
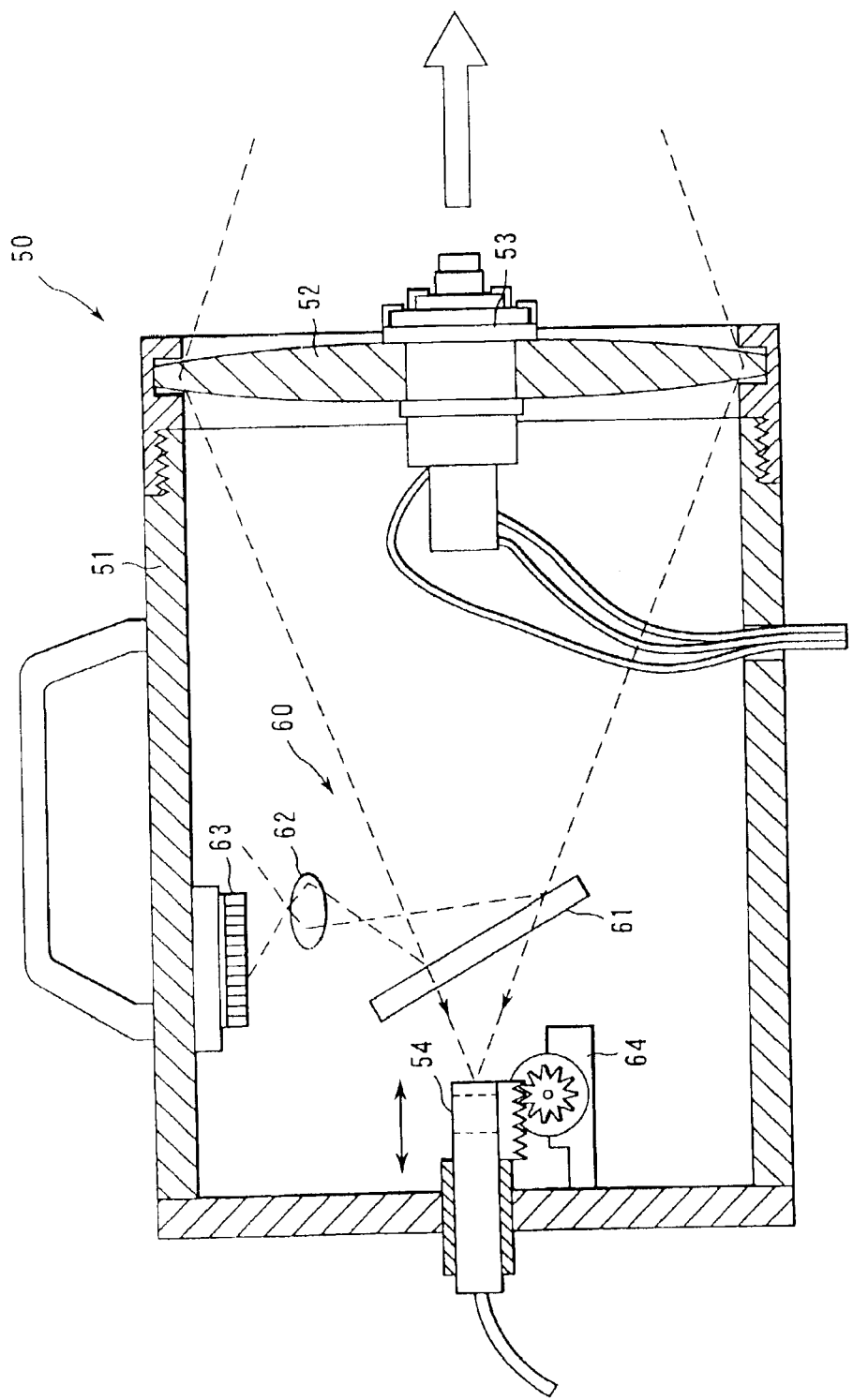
FIG. 14 is a side sectional view showing another structure of a conventional laser absorption spectroscopy type gas detecting device.

FIG. 11 is a front view showing the configuration of the laser absorption spectroscopy type gas detecting device 70 according to the sixth embodiment.

The concave mirror 16 as shown in FIG. 10 and FIG. 11 is such that the concave mirror 16 of the configuration as shown in FIG. 5B is disposed to be turned upside down.

Here, the housing 2 is formed in, for example, a rectangular parallelepiped box shape, and the handle 2a for carrying is provided at the upper portion thereof, and the housing 2 is freely carried.

At the front surface portion of the housing 2, the light transmitting portion 2b, in which, for example, a transparent resin body, a glass or the like is fitted into an opening portion formed so as to be a size equivalent to or greater than a diameter D/2 of the concave mirror 16, is formed.

Note that, in this sixth embodiment as well, the relationship of the measuring distance—the condensing position when the optical axis is provided at the center of the concave mirror 16 of FIG. 5B as shown in FIG. 6 described above, and the relationship of the offset amount ΔY, ΔZ of the concave mirror 16 of FIG. 5B as shown in FIG. 7 may be applied.

As shown in FIG. 10 and FIG. 11, in the laser absorption spectroscopy type gas detecting device 70, the light receiver 7 and the moving means 41 can be disposed at a position which is away from the region where incident light on the concave mirror 16 passes through.

According to such a configuration of the laser absorption spectroscopy type gas detecting device 70 of the sixth embodiment, a decrease in the light receiving level of the laser beam, scattered and reflected by the material body 9 having the property of reflecting external light and returning, can be prevented.

Further, in this sixth embodiment, the light source device 5 is formed from only the semiconductor laser module 5a, and the laser beam having a wavelength coinciding with an absorption spectrum which is particular to the gas to be detected is emitted to the exterior via the light transmitting portion 2b.

When the gas to be detected is methane gas, the semiconductor laser module 5a configuring the light source device 5 has a semiconductor laser (LD) generating laser beam of a wavelength band covering an absorption wavelength of 1.65 μm, and light emission driving means thereof, temperature controlling means and the like.

As shown in FIG. 10, the light source device 5 is configured from only the semiconductor laser module 5a provided at the rear portion of the central position of the concave mirror 16.

Further, the laser beam is directly emitted from this semiconductor laser module 5a.

This semiconductor laser module 5a emits the laser beam at the optical axis A1 via the opening portion 16 opened at the central position of the concave mirror 16.

In this case, a condensing lens (not shown) narrowing the laser beam generated by the LD into a beam shape is provided at the semiconductor laser module 5a.

Further, in this sixth embodiment as well, in the same way as in the fifth embodiment, the moving means 41 is provided in order to carry out adjustment of the offset of the condensing position (focal point adjustment) by adjusting the irradiated state of the visible light from the visible light source 30 with respect to the material body 9 having the property of reflecting external light.

Namely, because the laser beam emitted from the light source device 5 is invisible light, a user cannot directly view the irradiated state of the laser beam with respect to the gas to be detected.

Therefore, the emitting direction and the position of the laser beam from the light source device 5 must be set in advance, by separately emitting and image-forming the light from the visible light source 30 toward the material body 9 having the property of reflecting external light.

As described above, because the light receiver 7 is disposed at the condensing position P by the concave mirror 6, by using this arrangement, the moving means 41 changes the emitting surface of the visible light source 30 to the position of the light receiving surface of the light receiver 7.

For example, a point light source is used as the visible light source 30, and a small lamp bulb of a flashlight or the like can be used.

Here, the moving means 41 moves the light receiver 7 along the oblique direction X corresponding to the offset amounts Δ (ΔY, ΔZ).

This moving means 41 is configured from the biaxial rail member 22 holding the light receiver 7 and moving it respectively in the aforementioned oblique direction X and the widthwise direction of the housing 2 (direction V perpendicular to direction X), the supporting member 8 which is connected to a rail 22a at the sliding side and extends to the handle 2a portion of the housing 2, and the operating lever 12 which freely moves at the interior of the guide slot 2b of the handle 2a.

Note that the slot 23 which the supporting member 8 is inserted through is formed in a vertical direction.

Further, the light receiver 7 and the visible light source 30 are provided at the rail member 22 such that the light receiving surface of the light receiver 7 and the light emitting surface of the visible light source 30 are integrated to be directed in the same direction is formed at the rail 22a.

In accordance therewith, due to the light receiver 7 and the visible light source 30 freely sliding in the widthwise direction V of the housing 2, the light receiving surface of the light receiver 7 and the light emitting surface of the visible light source 30 can be replaced on the same position.

Note that, as illustrated, due to the supporting member 8 being connected to the light receiver 7 and visible light source 30 which have been made integral, there is a configuration in which movement in the widthwise direction V can be carried out by using the operating lever 12.

Further, the signal lines of the light receiver 7 and the visible light source 30 are configured so as to pass through the interior of the supporting member 8.

Next, confirmation of the laser irradiating position and focal point adjustment operation by using the visible light before the gas detecting operation will be described.

At the time of gas detection, first, the user, by operating the supporting member 8 of the moving means 41 in the widthwise direction V of the housing 2 by the operating lever 12, repositions the visible light source 30 to the position of the light receiver 7, and can direct it toward the reflecting surface 16a of the concave mirror 16.

Thereafter, if the visible light source 30 is turned on, the visible light from the visible light source 30 reaches, via the concave mirror 16, the material body 9 having the property of reflecting external light, and a predetermined image which can be viewed is formed on the material body 9 having the property of reflecting external light.

Thereafter, the user, by operating the operating lever 12 within the handle 2a along the direction of the optical axis A1, moves the light receiver 7 along the oblique direction X in which the offset amounts (ΔY, ΔZ) are combined, and can position the visible light source 30 at optimal condensing positions P corresponding to the respective measuring distances.

At this time, the user can operate the operating lever 12 while holding the handle 2a of the laser absorption spectroscopy type gas sensing device 70.

In this state, the visible light source 30 is positioned at the optimal condensing position by the concave mirror 16 corresponding to the distance to the material body 9 having the property of reflecting external light.

Accordingly, thereafter, the user, by moving the operating lever 12 in the widthwise direction V of the housing 2 and switching the visible light source 30 and the light receiver 7 again, can position the light receiver 7 at the optical condensing position P corresponding to the measuring distance.

Then, thereafter, the light source device 5 is driven and the laser beam is irradiated toward the place at which the gas to be detected exists. The laser beam, scattered and reflected by the material body 9 having the property of reflecting external light and returning, is condensed at the concave mirror 16 and is received at the light receiver 7, and gas detection is carried out.

In this state, the light receiver 7 is positioned at the optimal condensing position P corresponding to the measuring distance of the material body 9 having the property of reflecting external light.

Although the moving means 41 of the configuration is configured so as to move the light receiver 7 in the oblique direction X at the time of focal point adjustment to the condensing position P, conversely, there may be a configuration in which the light receiver 7 is fixed on the housing 2 and the concave mirror 16 is moved along the oblique direction X by the moving means 41, and the same operational effects can be obtained.

In this case, at the light receiver 7 side, the visible light source 30 is disposed at the side portion, and is configured so as to be replaceable by the rail member 22.

In the case of the structure moving the concave mirror 16, strictly, in light of the relationship of the optical axis, it is preferable for the concave mirror 16 and the light source device 5 to be integrated, and for these to be integrally moved.

In accordance with the laser absorption spectroscopy type gas detecting devices according to the fifth and sixth embodiments of the present invention as described above, because they are configured such that the light receiver and the visible light source can be interchanged at the condensing position of the concave mirror, the visible light showing the gas detecting direction can be image-formed on the material body having the property of reflecting external light, by using the visible light source.

In accordance therewith, the gas detecting operation by using the laser beam which is invisible light can easily proceed, and the gas detecting work can be smoothly performed.

Further, the light receiving surface of the light receiver can be positioned at the condensing position of the reflected light by the concave mirror merely by the simple operation in which the relative positions of the concave mirror and the visible light source are adjusted and the visible light source and the light receiver are switched so as to make the image-forming state of the visible light on the material body having the property of reflecting external light optimum by using the visible light source. Therefore, focal point adjustment can be easily carried out with a simple structure.

In this case, the condensing position is changed interlockingly with the change in the measuring distance.

However, due to the configuration in which the light receiver and the visible light source can be interchanged with respect to the concave mirror and are relatively movable, even if the measuring distance is changed, focal point adjustment, for positioning the light receiving surface of the light receiver on the optimal condensing position of the concave mirror, can be carried out in accordance with the change.

In accordance therewith, the optimal light receiving level is obtained, and stable gas detection can be always carried out.

Further, it is not limited to the configuration in which the moving means 41 is manually-operated by the user as described above.

For example, it may be configured such that the moving means 41 is configured from an actuator and the moving means 41 is automatically controlled by the processing device.

In this case as well, the processing device may be configured so as to, while moving the moving means 41, stop it at the position at which the maximum value of the light receiving level output from the light receiver 7 is detected.

Note that, with respect to the concave mirror described in the respective embodiments, although an example of a concave mirror whose reflecting surface is a paraboloid or ellipsoid based shape was described, the shape of the reflecting surface is not limited to these.

As the reflecting surface of the concave mirror, other than a paraboloid and an ellipsoid based shape, there are various types of shapes such as an off-axis ellipsoid based shape, a spherical surface based shape, an off-axis paraboloid shape and the like.

With respect to the concave mirror having any of these reflecting surfaces as well, by disposing the light receiver 7 on the theoretical focal point position, the laser absorption spectroscopy type gas detecting device, in which the laser beam reflected by the material body 9 having the property of reflecting external light and returning is condensed on the position of the light receiver 7 and gas detection is possible, can be configured.

Further, the measuring distance has a predetermined range and has the condensing position P which differs for each measuring distance with respect to the theoretical focal point distance F. Therefore, due to the laser absorption spectroscopy type gas detecting device in accordance with the present invention being configured so as to relatively move the light receiver or the concave mirror, even if the measuring distance is different, the condensing position of the reflected light can be positioned on the light receiving surface of the light receiver.

This moving direction can be obtained on the basis of the set items which are necessary for each concave mirror of the various types.

Further, in the laser absorption spectroscopy type gas detecting device described above, if the oscillating wavelength of the semiconductor laser is made to match the absorption spectrum of the gas to be detected, it can be applied to detection of various types of gases other than the methane gas such as carbon dioxide gas and acetylene gas.

Accordingly, as described above in detail, according to the present invention, the laser absorption spectroscopy type gas detecting device, which aims to be compact and lightweight and can be easily carried, can be provided.

Further, according to the present invention, the laser absorption spectroscopy type gas detecting device which is easily carried due to being made compact and lightweight and in which visual confirmation of the irradiating position of the laser beam and the focal point adjustment at the interior can be easily carried out, and a gas detecting method utilizing laser absorption spectroscopy including focal point adjustment of the device, can be provided.

What is claimed is:

1. A laser absorption spectroscopy type gas detecting device comprising:

a housing having a light transmitting portion;

a light source device which is disposed within the housing and which emits through the light transmitting portion a laser beam containing a light component having a wavelength corresponding to an absorption spectrum of a gas to be detected;

a concave mirror which is disposed within the housing and which has a reflecting surface that reflects the laser beam on a predetermined condensing position, after the laser beam has been reflected by a material body outside the housing and returned into the housing via the light transmitting portion;

a light receiver which is adapted to be disposed at a position within the housing at the condensing position, and which outputs an electric signal to detect whether the gas to be detected is present in a vicinity of the material body, in accordance with a degree of damping of the light component having the wavelength corresponding to the absorption spectrum of the gas to be detected, by receiving the laser beam which returns via the light transmitting portion;

a visible light source which is adapted to be disposed at a position within the housing at the condensing position and which by emitting visible light toward the concave mirror: (i) emits the visible light to the exterior via the light transmitting portion on a path in an opposite direction of the laser beam reflected by the material body and returning via the light transmitting portion, and (ii) forms a predetermined image which can be visually confirmed on the material body; and moving means for moving the positions of the light receiver and the visible light source so as to be interchanged.

2. A laser absorption spectroscopy type gas detecting device according to claim 1, wherein the moving means is configured so as to freely move and adjust a relative position of the concave mirror and the light receiver.

3. A laser absorption spectroscopy type gas detecting device according to claim 1, wherein the moving means is configured such that the light receiving surface of the light receiver and the light emitting surface of the visible light source can be interchanged on substantially the same position with respect to the concave mirror.

4. A laser absorption spectroscopy type gas detecting claim device according to claim 1, wherein the light source device comprises:

a semiconductor laser module which emits the laser beam, and which is provided out of an optical path of the laser beam returning via the light transmitting portion;

a fiber collimator which is provided at a position in front of the concave mirror, and which directs the laser beam emitted from the semiconductor laser module to outside of the housing along an optical axis positioned at a center of the concave mirror; and an optical fiber which leads the laser beam emitted from the semiconductor laser module to the fiber collimator.

5. A laser absorption spectroscopy type gas detecting device according to claim 1, wherein:

the light source device comprises a semiconductor laser module which emits the laser beam, and which is provide behind a central position of a concave mirror; and an opening portion, through which the laser beam emitted from the semiconductor laser module passes, is formed through the central position of the concave mirror.

6. A laser absorption spectroscopy type gas detecting device according to claim 1, wherein the reflecting surface of the concave mirror has one of a paraboloid shape and an ellipsoid based shape corresponding to a setting of a predetermined diameter D and a predetermined focal point distance F.

7. A laser absorption spectroscopy type gas detecting device according to claim 1, wherein the reflecting surface of the concave mirror has a shape of one of a paraboloid, a portion of an ellipsoid, and a portion of corresponding to a setting of a predetermined diameter D and a predetermined focal point distance F.

8. A gas detecting method utilizing laser absorption spectroscopy, comprising:

a step of emitting a laser beam containing a light component having a wavelength corresponding to an absorption spectrum of a gas to be detected, to the exterior by a light source device;

a step of making the laser beam, emitted to the exterior from the light source device and reflected by a material body existing in an advancing direction of the laser beam and having a property of reflecting light and returning it, be reflected and condensed on a predetermined condensing position by a concave mirror having a reflecting surface;

a step of detecting whether or not the gas to be detected exists at a front portion of the material body, in accordance with the degree of damping of the light component having the wavelength corresponding to the absorption spectrum of the gas to be detected, by receiving, at a light receiver opposing the concave mirror, the laser beam condensed on the condensing position by the concave mirror and reflected by the material body and returning; and a step of making, in advance of the detecting step, a predetermined image, which enables viewing of an irradiated position of the laser beam emitted from the light source device to the exterior, be formed on the material body, by opposingly disposing a visible light source emitting visible light instead of the light receiver which opposes the concave mirror and by emitting the visible light from the visible light source to the exterior.

9. A laser absorption spectroscopy type gas detecting method according to claim 8, further comprising:

a step of changing the relative position of the concave mirror and the visible light source such that an image-forming state of a predetermined image which can be viewed on the material body by the visible light from the visible light source is optimal, wherein the light receiving surface of the light receiver can be positioned at the condensing position of the reflecting light by the concave mirror, and focal point adjustment corresponding to the distance to the material body having the property of reflecting the external light is possible.

10. A laser absorption spectroscopy type gas detecting device comprising:

a housing having a light transmitting portion;

a light source device which is disposed within the housing and which emits through the light transmitting portion a laser beam containing a light component having a wavelength corresponding to an absorption spectrum of a gas to be detected;

a concave mirror which is disposed within the housing and which has a reflecting surface that reflects and condenses the laser beam on a predetermined condensing position, after the laser beam has been reflected by a material body outside the housing and returned into the housing via the light transmitting portion;

a light receiver which is disposed within the housing at the predetermined condensing position, and which outputs an electric signal to detect whether the gas to be detected is present in a vicinity of the material body, in accordance with a degree of damping of the light component having the wavelength corresponding to the absorption spectrum of the gas to be detected, by receiving the laser beam which returns via the light transmitting portion; and an adjustment mechanism for freely moving and adjusting a relative position of the concave mirror and the light receiver in accordance with a distance to the material body so that the light receiver is positioned at the condensing position.

11. A laser absorption spectroscopy type gas detecting device according to claim 10, wherein the light source device comprises:

a semiconductor laser module which emits the laser beam and which is provided out of an optical path of the laser beam returning into the housing via the light transmitting portion;

a fiber collimator which is provided at a position in front of the concave mirror, and which directs the laser beam emitted from the semiconductor laser module to outside of the housing along an optical axis which is positioned at a center of the concave mirror; and an optical fiber which leads the laser beam emitted from the semiconductor laser module to the fiber collimator.

12. A laser absorption spectroscopy type gas detecting device according to claim 10, wherein:

the light source device comprises a semiconductor laser module which emits the laser beam, and which is provided behind a central position of the concave mirror; and an opening portion is formed in the central portion of the concave mirror such that the laser beam emitted from the semiconductor laser module passes therethrough.

13. A laser absorption spectroscopy type gas detecting device according to claim 10, wherein the reflecting surface of the concave mirror has one of a paraboloid shape and an ellipsoid based shape, corresponding to a setting of a predetermined diameter D and a predetermined focal point distance F.

14. A laser absorption spectroscopy type gas detecting device according to claim 10, wherein the reflecting surface of the concave mirror has a shape of one of a paraboloid, a portion of an ellipsoid, and a portion of a paraboloid, corresponding to a setting of a predetermined diameter D and a predetermined focal point distance F.

15. A laser absorption spectroscopy type gas detecting device according to claim 10, wherein the adjustment mechanism comprises:

an operation member for moving a supporting member which positions the light receiver at the predetermined condensing position along an optical axis of the laser beam emitted by the light source device; and a guide section which guides the operation member along the optical axis.

16. A laser absorption spectroscopy type gas detecting device according to claim 10, wherein:

wherein the reflecting surface of the concave mirror has a shape of one of a paraboloid and a portion of an ellipsoid, corresponding to a setting of a predetermined diameter D and a predetermined focal distance F;

the light source device comprises a semiconductor laser module which emits the laser beam, and which is provided behind a central position of the concave mirror, and and opening portion is formed in the central portion of the concave mirror such that the laser beam emitted from the semiconductor laser module passes therethrough; and the light receiver is positioned at a position away from a region of transmission of the reflected light from the concave mirror as the predetermined condensing portion.

17. A laser absorption spectroscopy type gas detecting device according to claim 16, wherein the adjustment mechanism comprises:

a rail mechanism having a fixed and movable rail member for moving the light receiver in an oblique direction, while maintaining the position away from the region of transmission of the reflected light from the concave mirror as the predetermined position;

an operation member which is adapted to move a supporting member connected to the movable rail member on a rail mechanism side, along an optical axis of the axis of the laser beam emitted by the light source device, and a guide section which guides the operation member along the optical axis.

* * * * *

UNITED STATES PATENT AND TRADEMARK OFFICE
CERTIFICATE OF CORRECTION

PATENT NO. : 6,876,450 B2
DATED : April 5, 2005
INVENTOR(S) : Masaya Nanami

It is certified that error appears in the above-identified patent and that said Letters Patent is hereby corrected as shown below:

<u>Title page,</u>
Insert Item -- [30] Foreign Applications Priority Data:
                Jan 30, 2001 (JP) Japan ..... 2001-021941
                Jan 30, 2001 (JP) Japan ..... 2001-021942 --

Signed and Sealed this

Fifth Day of July, 2005

JON W. DUDAS
*Director of the United States Patent and Trademark Office*